(12) United States Patent
Kirkemo

(10) Patent No.: US 10,918,365 B2
(45) Date of Patent: *Feb. 16, 2021

(54) MEDICAL RETRIEVAL SYSTEMS AND RELATED METHODS

(71) Applicant: Boston Scientific Scimed, Inc., Maple Grove, MN (US)

(72) Inventor: Aaron Kirkemo, Gladstone, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/231,163

(22) Filed: Dec. 21, 2018

(65) Prior Publication Data

US 2019/0133564 A1 May 9, 2019

Related U.S. Application Data

(63) Continuation of application No. 14/863,858, filed on Sep. 24, 2015, now Pat. No. 10,194,893.

(Continued)

(51) Int. Cl.
*A61B 17/00* (2006.01)
*A61B 1/00* (2006.01)
(Continued)

(52) U.S. Cl.
CPC ...... *A61B 17/00234* (2013.01); *A61B 1/0052* (2013.01); *A61B 1/0053* (2013.01); *A61B 1/0055* (2013.01); *A61B 1/00133* (2013.01); *A61B 1/00154* (2013.01); *A61B 1/307* (2013.01); *A61B 17/221* (2013.01); *A61B 17/3417* (2013.01); *A61M 25/0113* (2013.01); *A61B 2017/003* (2013.01);
(Continued)

(58) Field of Classification Search
CPC ............ A61B 1/00133; A61B 1/00154; A61B 1/0052; A61B 1/0053; A61B 1/0055; A61B 1/307; A61B 17/00234; A61B 17/221; A61B 17/3417; A61B 2017/00367; A61B 2017/00407; A61B 2017/0042; A61B 2017/00424; A61B 2017/00477; A61B 2017/00738; A61B 2017/00991; A61M 25/0113
See application file for complete search history.

(56) References Cited

U.S. PATENT DOCUMENTS 4,557,255 A 12/1985 Goodman
4,598,698 A 7/1986 Siegmund
(Continued)

OTHER PUBLICATIONS

International Search Report and Written Opinion for International Application No. PCT/US2015/052134, dated Dec. 8, 2015 (10 pages).

*Primary Examiner* — Jocelin C Tanner
(74) *Attorney, Agent, or Firm* — Bookoff McAndrews, PLLC

(57) ABSTRACT

A medical device may include a stabilizer configured to be coupled to a port of an insertion device. The medical device may further include a shaft configured for telescopic translation within the stabilizer and a grip coupled to the shaft. Further, the medical device may include an actuator coupled to the grip. The actuator may be axially moveable relative to the grip so as to selectively actuate a distal assembly of the medical device.

18 Claims, 20 Drawing Sheets

Related U.S. Application Data

(60) Provisional application No. 62/056,303, filed on Sep. 26, 2014.

(51) Int. Cl.
*A61B 17/34* (2006.01)
*A61M 25/01* (2006.01)
*A61B 1/005* (2006.01)
*A61B 1/307* (2006.01)
*A61B 17/221* (2006.01)

(52) U.S. Cl.
CPC ........... *A61B 2017/0042* (2013.01); *A61B 2017/00367* (2013.01); *A61B 2017/00407* (2013.01); *A61B 2017/00424* (2013.01); *A61B 2017/00477* (2013.01); *A61B 2017/00738* (2013.01); *A61B 2017/00991* (2013.01)

(56) References Cited

U.S. PATENT DOCUMENTS

| | | | |
|---|---|---|---|
| 5,408,991 | A | 4/1995 | Iida et al. |
| 6,193,672 | B1 | 2/2001 | Clement |
| 8,075,478 | B2 | 12/2011 | Campos |
| 8,409,168 | B2 | 4/2013 | Wondka et al. |
| 10,194,893 | B2 * | 2/2019 | Kirkemo ............... A61B 1/0052 |
| 2005/0182292 | A1 | 8/2005 | Suzuki |
| 2005/0222557 | A1 | 10/2005 | Baxter et al. |
| 2006/0224041 | A1 | 10/2006 | Okada |
| 2008/0172038 | A1 | 7/2008 | Dollar et al. |
| 2009/0005792 | A1 * | 1/2009 | Miyamoto ......... A61B 17/0487 |
| | | | 606/139 |
| 2009/0259105 | A1 | 10/2009 | Miyano et al. |
| 2010/0191050 | A1 | 7/2010 | Zwolinski |
| 2010/0217184 | A1 | 8/2010 | Koblish et al. |
| 2012/0123204 | A1 | 5/2012 | Wynberg |
| 2012/0172850 | A1 * | 7/2012 | Kappel ................. A61B 90/50 |
| | | | 606/1 |

* cited by examiner

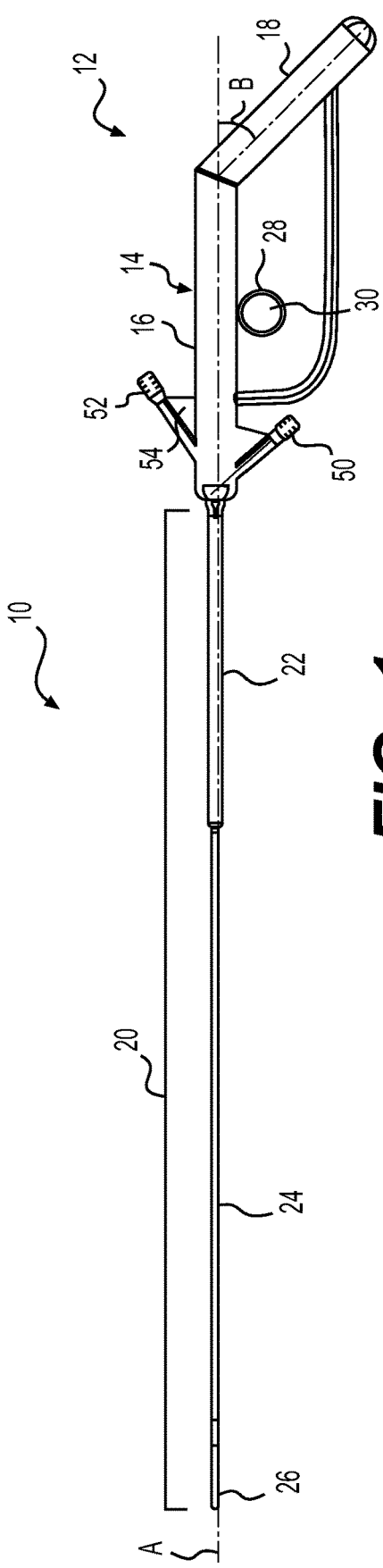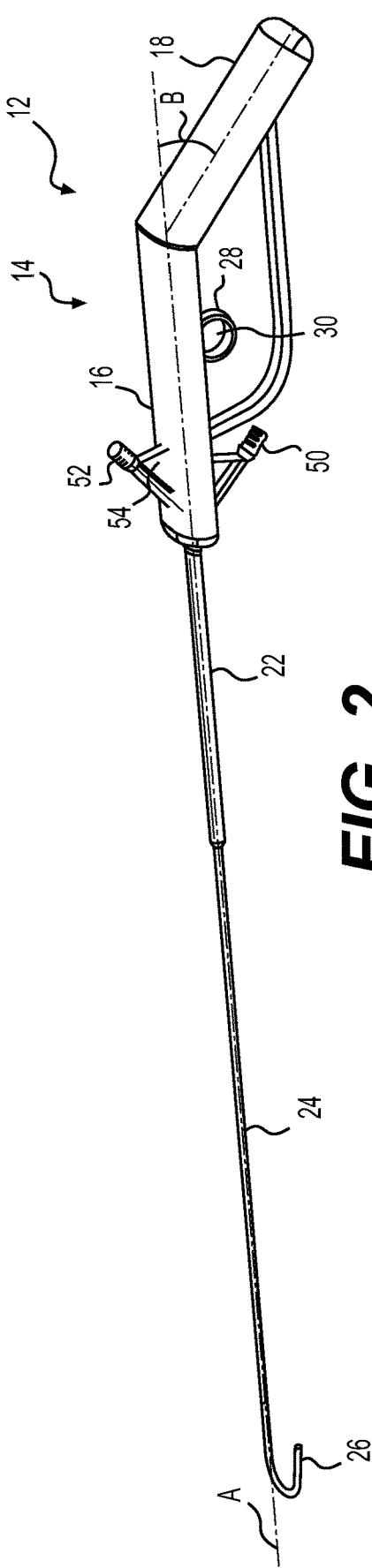

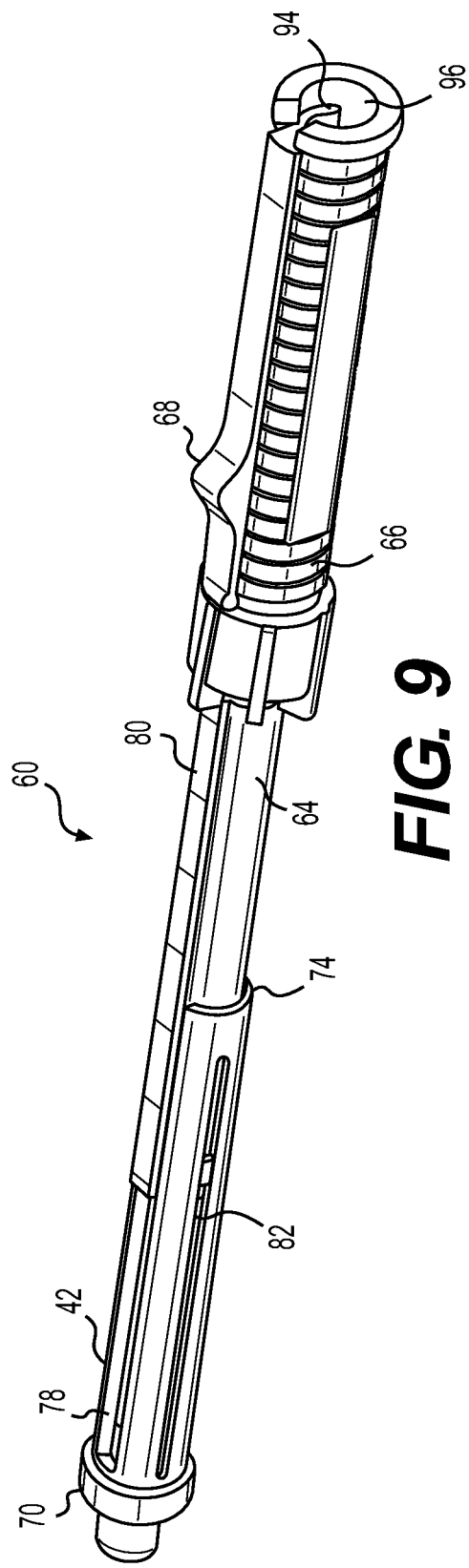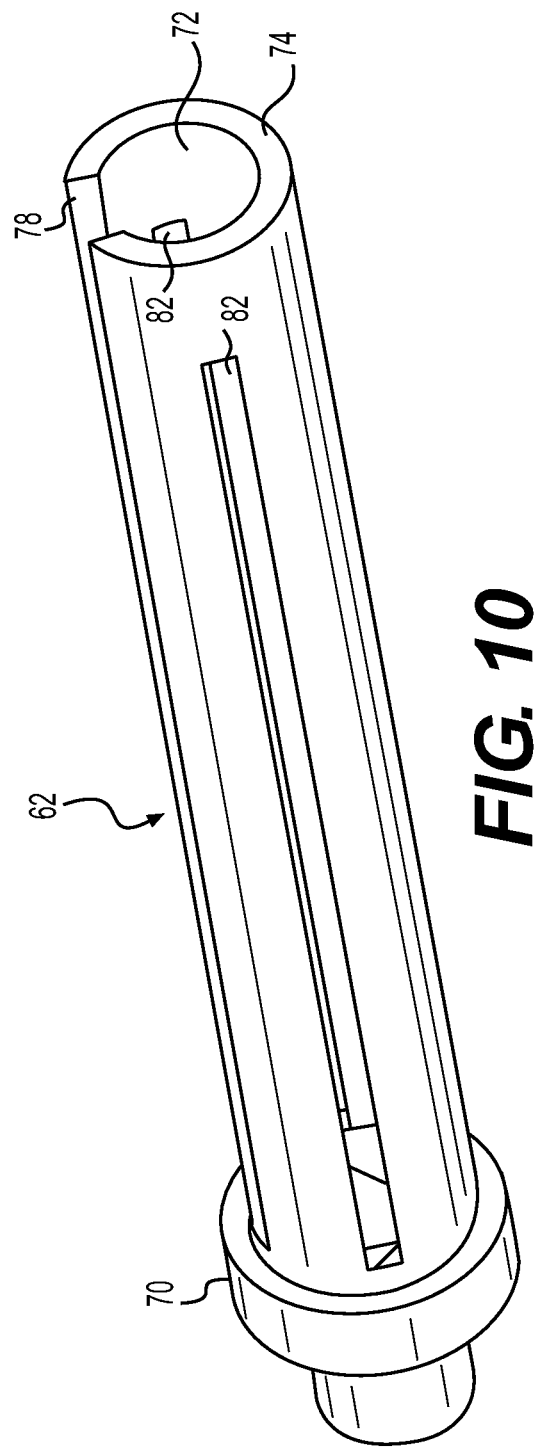

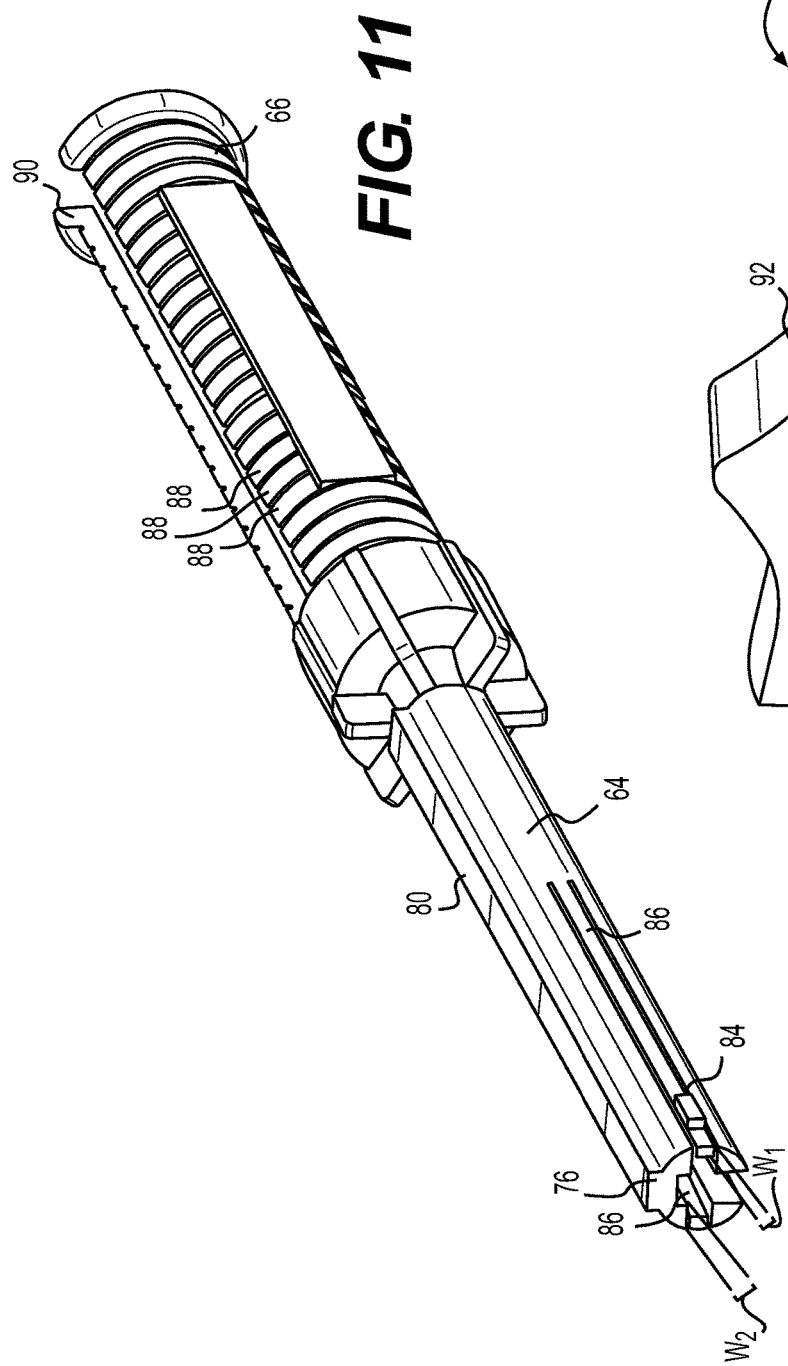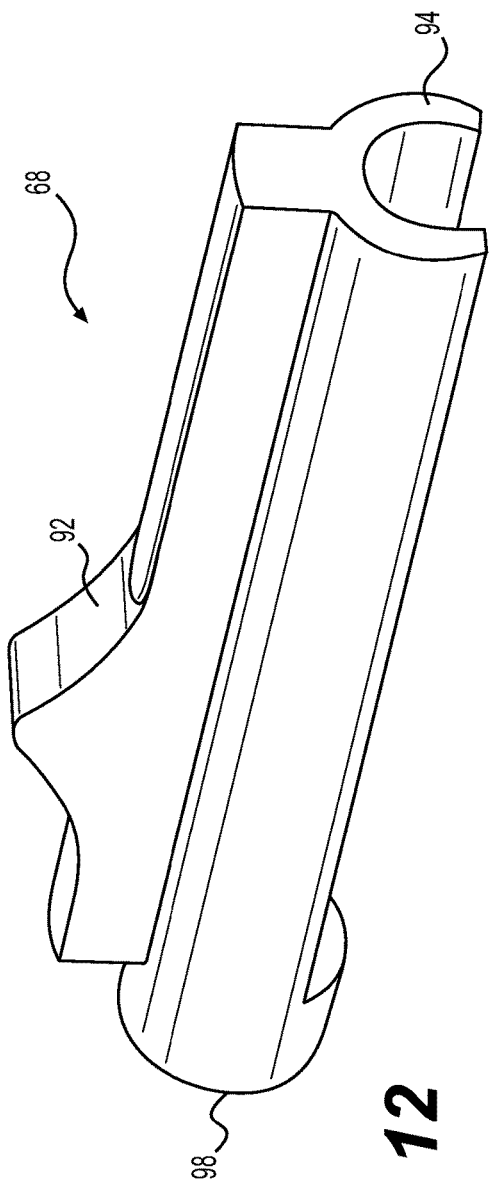

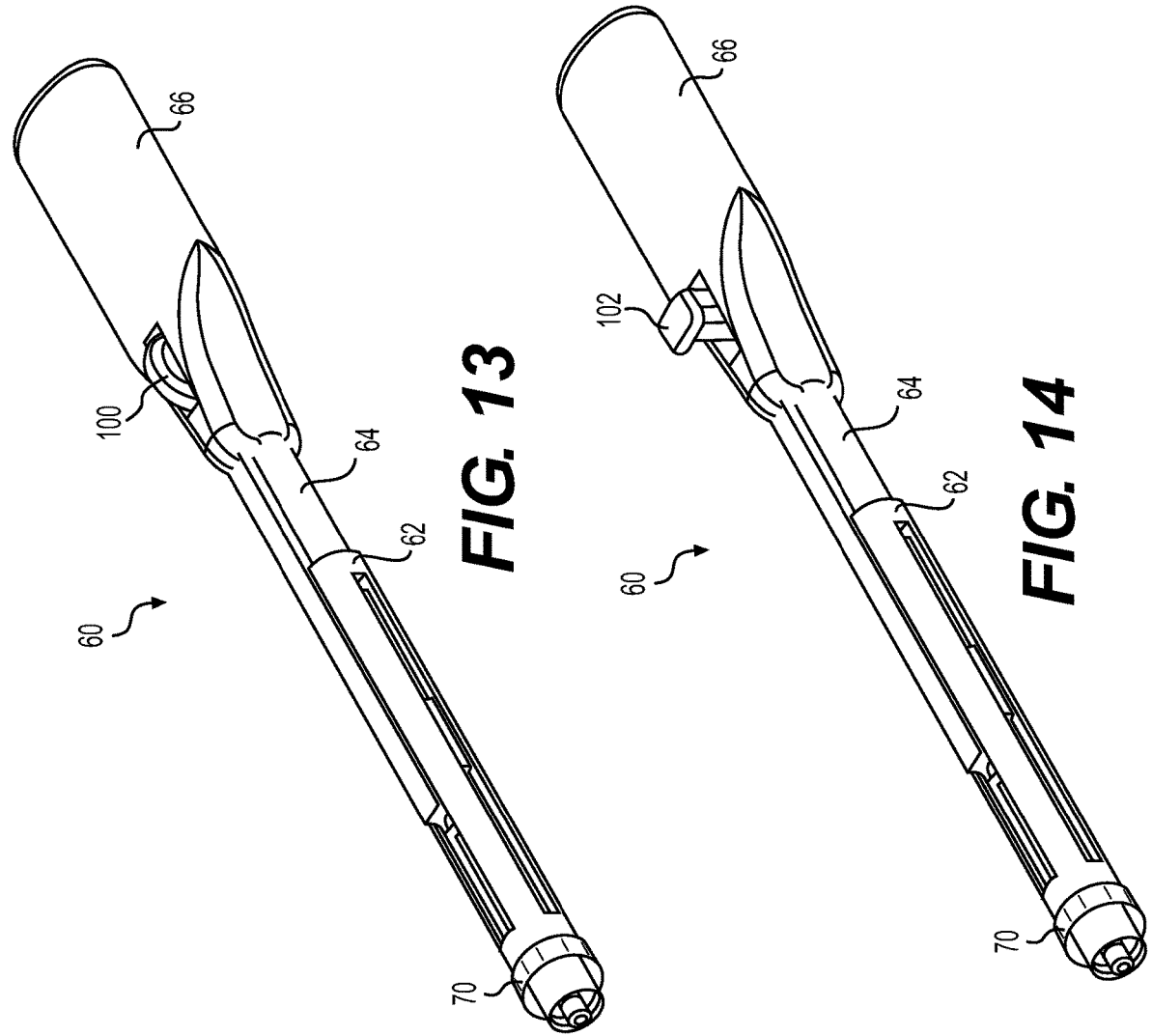

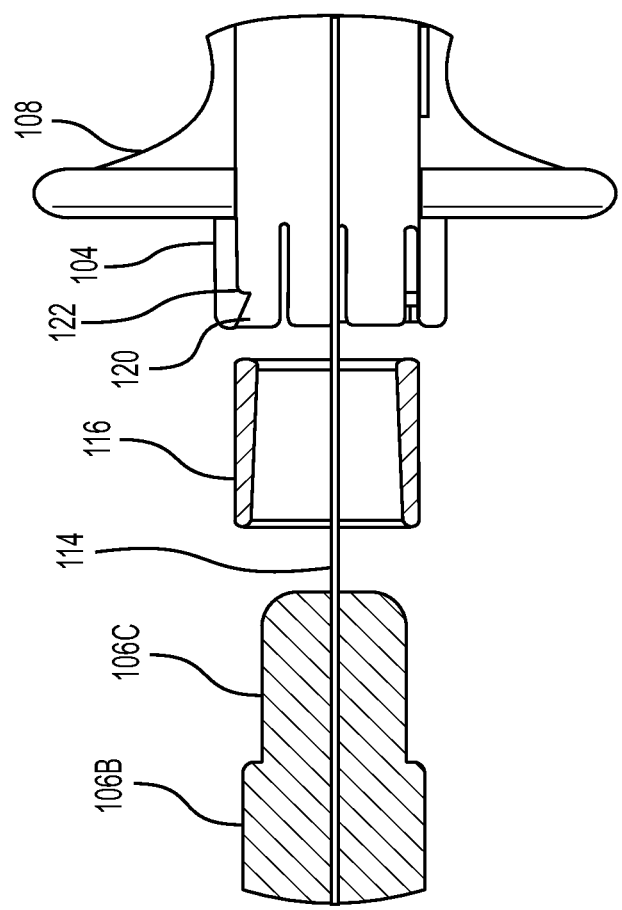

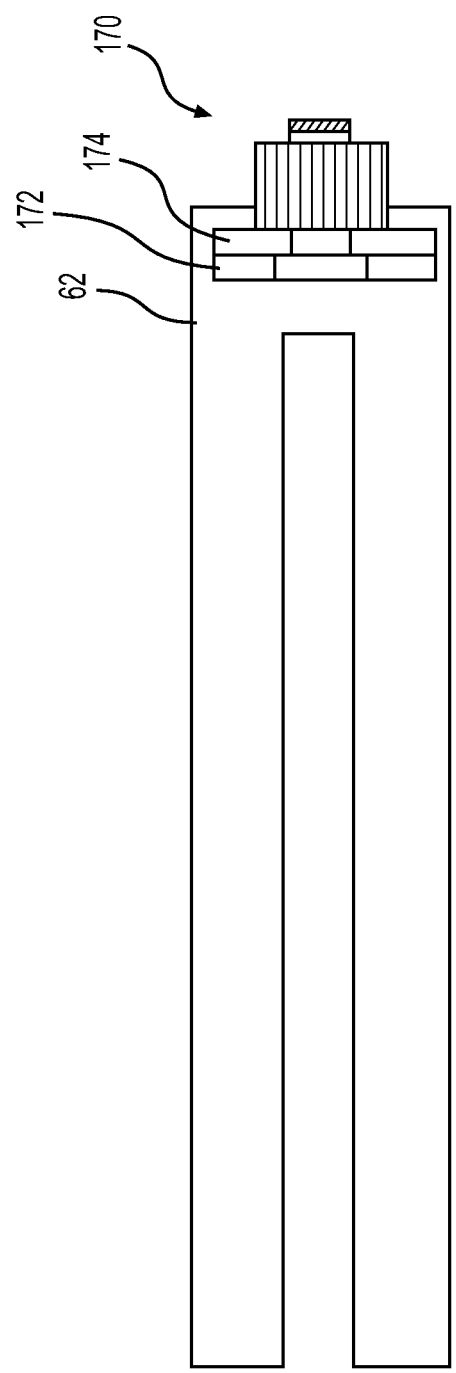

MEDICAL RETRIEVAL SYSTEMS AND RELATED METHODS

CROSS-REFERENCE TO RELATED APPLICATIONS

This application is a continuation of U.S. application Ser. No. 14/863,858, filed Sep. 24, 2015, which claims the benefit of priority from U.S. Provisional Application No. 62/056,303, filed on Sep. 26, 2014, the entirety of each of which is incorporated herein by reference.

TECHNICAL FIELD

Various aspects of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Retrieval devices are also used in lithotripsy and ureteroscopy procedures to treat urinary calculi (e.g., kidney stones) in the ureter of a patient.

Ureteroscopy, for example, may be performed to diagnose and treat urinary tract diseases and ureteral strictures. A ureteroscope may be inserted retrograde through the urinary tract such that diagnosis and treatment of urinary tract abnormalities may be performed. Current flexible ureteroscopes require two hands to control the ureteroscope. Usually, the dominant hand will hold the handle of the ureteroscope while the non-dominant hand holds the distal portion of the ureteroscope as it enters the urethral meatus. If the medical professional determines there is a need to insert a tool such as a basket, grasper, or forceps through the working channel of the scope, he or she is left to either remove the non-dominant hand from the urinary meatus or instruct an assistant to hold the tool handle.

Removing their hand from the urinary meatus, however, removes the medical professional's ability to control the depth of the scope's insertion into the urinary meatus. On the other hand, if the medical professional opts to instruct an assistant to control the medical tool, for example, a basket, communication between the medical professional and assistant must be exact and clear, otherwise, the assistant may be required to perform multiple attempts at grasping a stone or other material before successfully capturing the stone or other material within the basket. Multiple attempts frequently result in damaged baskets, increased risk of damage to the patient's surrounding tissue, and increased time of procedure, among others.

In addition, conventional ureteroscopes are designed to be held in the vertical or upright position which necessitates that the medical professional tightly flex his or her arm at the elbow to bring their forearm parallel to their body and bend their wrist outward to grasp the ureteroscope. Distal tip scope deflection may be achieved via an actuator on the proximal end of the scope by the medical professional's index finger or thumb. As the medical professional rotates the ureteroscope, he or she may experience wrist angulation resulting in painful symptoms similar those of carpal tunnel. Holding the ureteroscope in such an upright position may also interfere with the medical professional's intuitive connection between the motion of their hand, and the resultant motion of a distal tip of the ureteroscope. It also precludes them from controlling the depth and rotation of any instrument inserted into the ureteroscope and the depth of the scope at the same time. End deflection and scope rotation is controlled by the dominant hand. The assistant manages the mechanical actuation of the instrument (opening and closing of graspers, baskets, scissors, loops, etc.).

The systems and methods of the current disclosure may rectify some of the deficiencies described above.

SUMMARY

Examples of the present disclosure relate to, among other things, medical retrieval systems and related methods of use. Each of the examples disclosed herein may include one or more of the features described in connection with any of the other disclosed examples.

In one example, a medical device may include a stabilizer configured to be coupled to a port of an insertion device. The medical device may further include a shaft configured for telescopic translation within the stabilizer and a grip coupled to the shaft. Further, the medical device may include an actuator coupled to the grip. The actuator may be axially moveable relative to the grip so as to selectively actuate a distal assembly of the medical device.

Examples of the medical device may additionally and/or alternatively include one or more of the following features: the stabilizer may include at least one longitudinally extending slot; the shaft may include at least one protrusion configured to be received within the at least one longitudinally extending slot; the shaft may be coupled to the stabilizer in a snap-fit arrangement; the stabilizer may include a longitudinally extending opening configured to receive a longitudinally extending extension of the shaft; the shaft may include at least one flex arm; the shaft may include at least two flex arms; the actuator may include at least one arm, wherein the arm may have an external surface configured to matingly cooperate with an internal surface of the grip; the actuator may include at least two arms, wherein each of the at least two arms may have an external surface configured to matingly cooperate with an internal surface of the grip; the stabilizer may be configured to be rotatably coupled to an insertion device; a coupler which may be fixedly coupled to the stabilizer and removably coupled to the insertion device; the shaft may be configured to be selectively prevented from axially moving relative to the stabilizer; the actuator may include a raised finger or thumb rest; a cross-sectional shape of the shaft may be U-shaped; and an exterior surface of the shaft may be configured to be matingly received within an interior surface of the stabilizer.

In another example, a system may include an insertion device. The insertion device may include a tubular member extending along a longitudinal axis. The tubular member may include a deflectable distal portion. The insertion device may also include a pistol-grip handle coupled to the tubular member. The pistol-grip handle may include a port configured to receive a medical device. The system may further include a medical device including a distal assembly and a proximal handle. The proximal handle may include a stabilizer configured for coupling with the port, a shaft telescopically coupled to the stabilizer, and an actuator configured to manipulate the distal assembly.

Examples of the system may additionally and/or alternatively include one or more of the following features: the tubular member may further include a proximal portion coupled to the pistol-grip handle and a medial portion positioned between the proximal portion and the deflectable distal portion, wherein the proximal portion is more rigid than the medial portion and the deflectable distal portion, and wherein the medial portion is more rigid than the deflectable distal portion; the proximal portion and the medial portion may extend along a longitudinal axis of the tubular member; the insertion device may further include an actuator operatively coupled to the deflectable distal portion, wherein distal advancement of the actuator may cause deflection of the deflectable distal portion in a first direction, and wherein proximal retraction of the actuator may cause deflection of the deflectable distal portion in a second direction, opposite of the first direction; the port may be a first port and may be positioned along a first surface of the pistol-grip handle, the insertion device may further include a second port positioned along either a second side of the pistol-grip handle opposite the first surface or on a proximalmost end of the pistol-grip handle; the proximal handle may be rotatably coupled to the port; and the shaft may be coupled to the stabilizer in a snap-fit arrangement.

In a further example, a method may include delivering an insertion device into an anatomical opening. The insertion device may include a tubular member extending along a longitudinal axis and having a deflectable distal portion. The insertion device may further include a port coupled to a medical device having a stabilizer and a shaft telescopically coupled to the stabilizer. The method may further include manipulating the deflectable distal portion. The method may also include distally advancing the shaft relative to the stabilizer and actuating a distal assembly of the medical device.

Examples of the system may additionally and/or alternatively include one or more of the following features: medical device may be rotatably coupled to the port; the insertion device may further include an actuator operatively coupled to the deflectable distal portion and the method may further include at least one of distally advancing the actuator to cause deflection of the deflectable distal portion in a first direction, and proximally retracting the actuator to cause deflection of the deflectable distal portion in a second direction, opposite of the first direction; and snap-fit connecting the stabilizer to the shaft.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIG. 1 depicts an insertion device according to an example of the disclosure;

FIG. 2 depicts the insertion device of FIG. 1 in a bent configuration;

FIG. 9 is an isometric view of the exemplary medical device handle of FIG. 8;

FIG. 10 depicts an exemplary stabilizer of the medical device handle of FIG. 8;

FIG. 11 depicts an exemplary grip and telescopic shaft of the medical device handle of FIG. 8;

FIG. 12 depicts an exemplary actuator of the medical device handle of FIG. 8;

FIG. 13 depicts an additional exemplary actuator of a medical device handle;

FIG. 14 depicts another exemplary actuator of a medical device handle;

FIGS. 17A-17C illustrate various views of another exemplary actuator of a medical device handle;

FIGS. 22A and 22B depict an exemplary rotational watertight coupling for use with any of the insertion devices of FIGS. 1-7 and the medical device handles of FIGS. 8-19.

DETAILED DESCRIPTION

Overview

Figure 3:
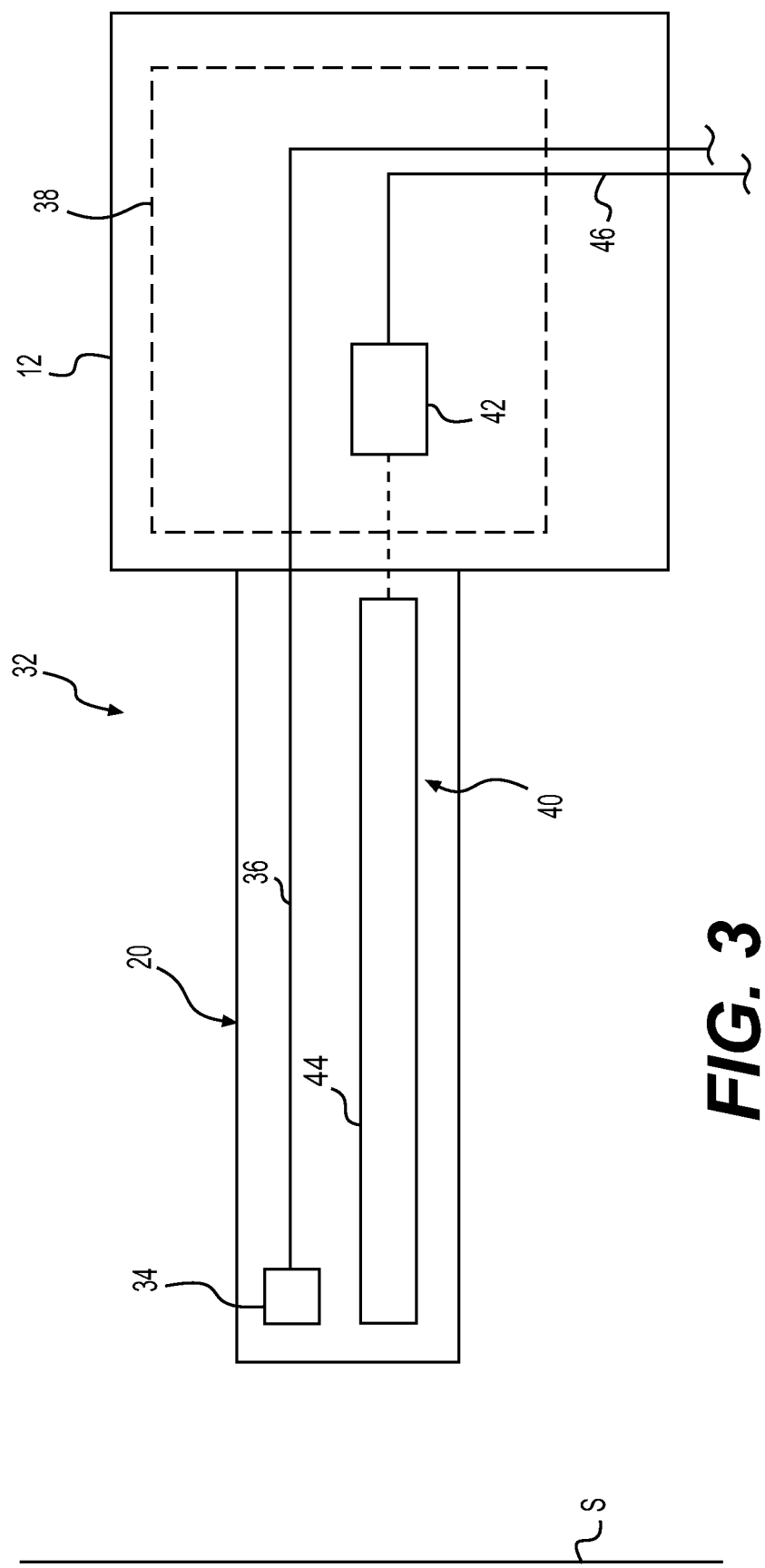
FIG. 3 schematically depicts exemplary imaging and illumination assemblies of the insertion device of FIG. 1.

Examples of the present disclosure relate to a medical system for diagnosing and/or treating internal areas of a subject's body. The medical system may include a medical device and an insertion device for facilitating ergonomic manipulation and intuitive control by a medical professional during a procedure.

Detailed Examples

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

FIG. 1 shows an exemplary scope and/or insertion device 10. Insertion device 10 may include any device configured to allow a user to perform medical diagnoses and/or treatments on a subject. For example, insertion device 10 may include any device configured to allow a user to access and view internal areas of a subject's body. Additionally or alternatively, insertion device 10 may include any device configured to deliver medical instruments, such as, for example, biopsy forceps, graspers, baskets, snares, probes, scissors, retrieval devices, lasers, and/or other tools, into a subject's body. Insertion device 10 may be inserted into a variety of body openings, lumens, and/or cavities. For example, insertion device 10 may be inserted into any portion of a urinary tract, such as a ureter, a gastrointestinal lumen, such as an esophagus, a vascular lumen, and/or an airway.

According to aspects of the present disclosure, insertion device 10 may be a ureteroscope. In some contemplated examples, insertion device 10 may be a sterile, single-use, and disposable ureteroscope. Alternatively, insertion device 10 may be a multiple-use, non-disposable ureteroscope. Other types of devices, however, may be substituted for the ureteroscope, including, as examples, an endoscope, a hysteroscope, a uteroscope, a bronchoscope, a cystoscope, and similar devices. Such devices may be single-use and disposable, or multiple-use and non-disposable.

Insertion device 10 may include a handle assembly 12. Handle assembly 12 may include a handle housing 14. Handle housing 14 may include a first portion 16 and a second portion 18. As shown in FIG. 1, the first portion 16 may extend along a longitudinal axis A of the insertion device 10, while the second portion 16 may extend at an angle B with respect to longitudinal axis A. For example, in some examples, angle B may be about 45°. In other examples, angle B may be between about 0° and 90°, between about 20° and 70°, or between about 35° and 55°. It is understood that the terms "about," "substantially," and "approximately," as used in this disclosure, include a range of plus or minus 5%.

The angled configuration of the handle assembly 12 provides numerous benefits. For example, since a medical professional is able to hold the handle assembly 12 in line with their forearm in a natural position (e.g., across their waist), the handle assembly 12 decreases carpal tunnel strain. Additionally, the pistol-like grip of handle assembly 12 enables an ergonomic grasping of insertion device 10 making manipulation of the insertion device increasingly comfortable and user-friendly by keeping the medical professional's wrist in line with longitudinal axis A of insertion device 10 during rotation and other manipulation of insertion device 10. The angled or pistol-like grip of handle assembly 12 additionally enables greater rotational freedom along longitudinal axis A as a medical professional can generally rotate his or her arm through a larger range of motion when held in the natural position with their wrist in line with longitudinal axis A rather than held upright with their wrist sharply bent with respect to longitudinal axis A. Finally, the angled or pistol-like grip of the handle assembly 12 may be universally grasped by the medical professional's hand, whether or not they are right-handed or left-handed, thus removing the need for specialized instruments for different medical professionals.

The handle assembly 12 may be formed in any appropriate manner. For example, two half-portions may be joined together by appropriate fasteners, such as, removable fasteners including screws and/or pins, or by non-removable fastening techniques, including heat bonding or adhering with an adhesive. Alternatively, handle assembly 12 may be extruded as a one-piece monolithic construction.

Insertion device 10 may also include a longitudinally extending tubular member 20 operably connected to handle assembly 12. Tubular member 20 may include, for example, a catheter, and may be configured to be at least partially inserted into a subject's body and navigated to an internal area therein. Tubular member 20 may be semi-rigid. For example, tubular member 20 may include one or more portions that are flexible, while others are substantially rigid. Its flexibility may allow tubular member 20 to be maneuvered into, through, and out of the subject's body. Tubular member 20 may be configured, for example, to traverse tortuous anatomical lumens of the subject's body.

For example, tubular member 20 may include a proximal portion 22, a medial portion 24, and a distal portion 26. The length of the proximal portion 22 may be approximately 12 to 25 cm long and be about 10 to 18 French (6 mm) in diameter; the length of the medial portion 24 may be approximately 20 to 30 cm long and be about 7 to 8 French (2.3 to 2.7 mm) in diameter; and the length of the distal portion 26 may be approximately 6 cm long and be about 7 to 8 French (2.3 to 2.7 mm) in diameter. It is understood, however, that larger or smaller dimensions may be appropriate for some patients and are within the scope of this disclosure. The proximal, medial, and distal portions 22, 24, and 26, may have cross-sectional configurations that are substantially uniform along their lengths, but they may taper distally. In other examples, the cross-sectional shape may vary along their length. For example, in some examples, proximal portion 22 may have an ovular cross-section shape while distal portion 26 and/or medial portion 24 have a circular cross-sectional shape. Other sizes, shapes, and arrangements are contemplated and within the scope of this disclosure.

Given the increased size (e.g., diameter) of proximal portion 22 relative to medial portion 24 and distal portion 26, proximal portion 22 may be considered a "rigid" portion and provides sufficient strength and rigidity to permit use within the bladder of a patient and to support the entry of the distal portion 26 and medial portion 24 into a ureter or other anatomical passage. Accordingly, proximal portion 22 may add robustness to insertion device 10 and prevent unintended flexion of tubular member 20 while within one or more of the urethra, prostatic fossa, and bladder neck of a patient.

Meanwhile, the medial portion 24, due to its decreased size (e.g., diameter) relative to proximal portion 22, and due to its increased size (e.g., diameter) relative to distal portion 26, may be considered a "semi-rigid" portion and provides numerous benefits. First, medial portion 24 may enhance the rotational response or insertion depth response of insertion device 10 when a medical professional rotates or distally advances handle assembly 12, and therefore, tubular member 20. Additionally, medial portion 24 eliminates the need for the medical professional to hold the insertion device 10 with his/her non-dominant hand at the urethral meatus to control insertion device 10 depth, thereby freeing a hand of the medical professional for other purposes. Additionally, due to its semi-rigid construction, medial portion 24 may enhance durability during a procedure, and/or during sterilization if reused.

The distal portion 26, due to its decreased size (e.g., diameter) relative to the proximal portion 22 and the medial portion 24, may be considered a "flexible" portion and may be manipulated as needed during a procedure, as will be described in further detail below. Since the insertion device 10 is designed to be held in line with the longitudinal axis A of the tubular member 20, the length of distal portion 26 may be largely reduced relative to conventional insertion devices.

Handle assembly 12 may further include an actuator 28 for manipulating distal portion 26. For example, actuator 28 may include a ring, button, and/or trigger configured to be proximally retracted and/or distally advanced by a finger of the medical professional. The actuator 28 may be mechanically coupled to (e.g., via a push/pull wire and/or cable) or otherwise cooperate (e.g., via an electrical servomotor) with the distal portion 26 of tubular member 20. For example, as shown in FIG. 1, actuator 28 may include a circular hole or opening 30, through which an index or other finger of a medical professional may be inserted. Upon urging actuator 28 in the distal direction, distal portion 26 may be caused to bend and/or flex in a first direction, as shown in FIG. 2. Upon urging actuator 28 in the proximal direction, distal portion 26 may be caused to bend and/or flex in a second direction, opposite the first direction. In such a manner, distal portion 26 may be moved, angled, or otherwise manipulated in a first and a second direction within a plane so as to direct the distal portion 26 as needed during a procedure. Such control may aid the medical professional in directing a medical device passed through the tubular member 20 of insertion device 10 to a specific location within a patient.

The distal portion 26 may be operatively coupled to the actuator 28 in any appropriate manner. For example, push/pull wires or other longitudinally extending members (not shown) may extend through conduits which extend longitudinally through tubular member 20. A proximal end of the push/pull wires may be coupled to the actuator 28, while a distal end may be anchored near, on, or within the distal portion 26 such that manipulation of the actuator 28 may cause distal portion 26 bend, move, or flex as shown in FIG. 2. For example, moving the actuator in a distal direction may cause one push/pull wire to be relaxed while another push/pull wire may be tensioned thereby causing the distal portion 26 to bend towards the tensioned push/pull wire, and vice versa. Alternative mechanisms may be used to manipulate distal portion 26 without departing form the scope of this disclosure. In some examples, linkages, rack and pinion arrangements, reversing rack and pinion arrangements, electro-mechanical, and/or electrical components may be used to cause distal portion 26 to bend in either the first or second directions.

In examples in which a reversing rack and pinion arrangement is used, a medical professional may choose whether he or she would like to follow the European standard (e.g., where a downward motion on an actuator results in an upward deflection, and vice versa) or U.S. standard (e.g., where a downward motion on an actuator results in a downward deflection, and vice versa). In such cases, and referring to FIGS. 21A and 21B, a rack gear system 300 may be attached to actuator 28 and include a moveable reversing rack gear 310 including an upper rack 310A and a lower rack 310B moveably coupled to an actuator rack 320. The rack gear system 300 may further include an actuator pinion 330 including a common drive shaft 340 with a reversing pinion 350. Further, reversing rack gear 310 may be coupled to and/or include a linkage 360 which may be coupled to distal portion 26 via one or more push/pull wires or other longitudinally extending members (not shown).

Figure 21A:
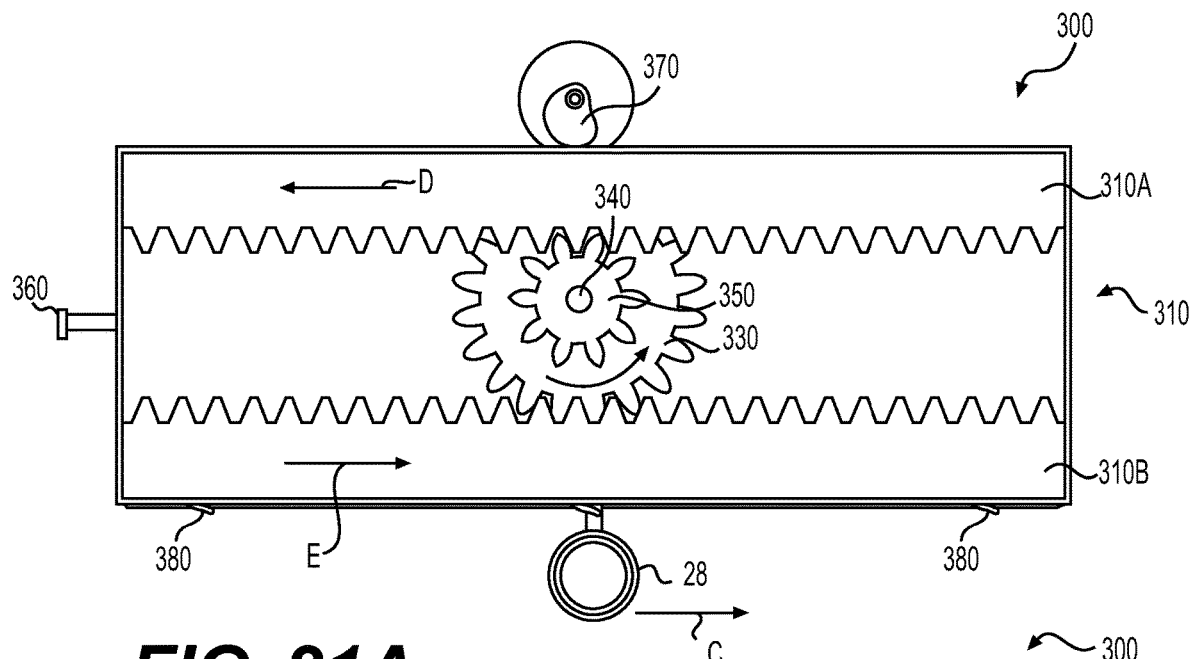
FIGS. 21A and 21B depict an exemplary reversing mechanism of the insertion device of FIG. 1.
Figure 21B:
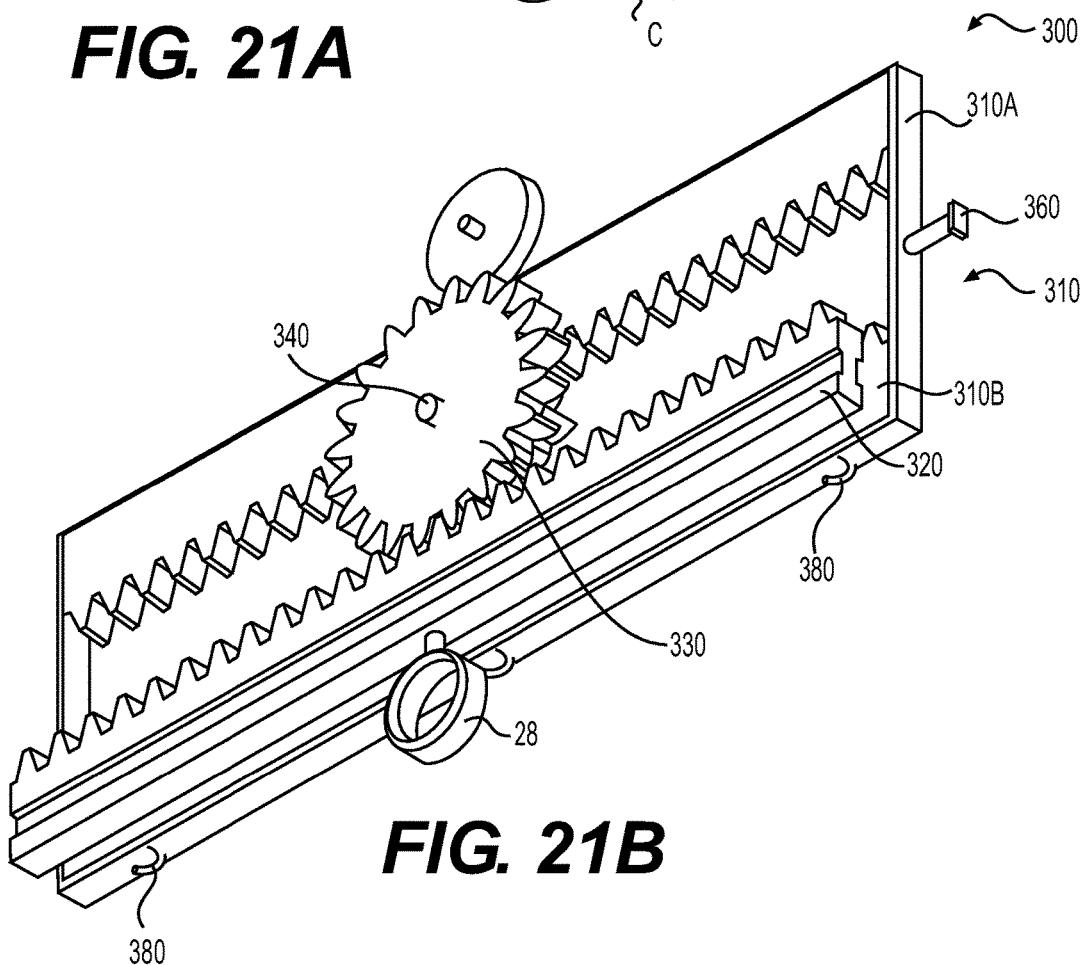

As shown in FIG. 21A, reversing rack gear 310 may be positioned such that an adjustment mechanism, such as eccentric cam 370, may adjust which of upper rack 310A and lower rack 310B engage with reversing pinion 350. For example, in the position shown in FIG. 21A, eccentric cam 370 is positioned downward so as to urge reversing rack gear 310 downward, thereby enabling teeth of upper rack 310A to operably engage teeth of reversing pinion 350 while teeth of lower rack 310B are free from engagement with teeth of reversing pinion 350. As shown in FIGS. 21A and 21B, reversing rack gear 310 may be spring-loaded or biased (e.g., via one or more springs 380 shown in a compressed configuration) such that when eccentric cam 370 is rotated 180° from the position shown in FIG. 21A, eccentric cam 370 no longer urges reversing rack gear 310 downward and springs 380 return towards an uncompressed state thereby urging teeth of lower rack 310B to operably engage teeth of reversing pinion 350 while teeth of upper rack 310A are free from engagement with teeth of reversing pinion 350. Eccentric cam 370 may be adjusted through any appropriate means, such as, for example, an adjustment wheel or slide actuator on handle assembly 12.

In use, a medical professional may adjust the eccentric cam 370 in a desired orientation, such as, for example, the downward orientation shown in FIG. 21A. Accordingly, reversing rack gear 370 may be urged downward such that teeth of upper rack 310A engage with teeth of reversing pinion 350. In use, the medical professional may cause actuator 28 to move in direction C as depicted by the arrow in FIG. 21A. Actuator 28 may be directly coupled to or monolithically formed with actuator rack 320 such that actuator rack 320 is urged in the same direction C. As actuator rack 320 is urged in direction C, teeth of actuator rack 320 may engage teeth of actuator pinion 330 thereby rotating actuator pinion 330 in the counter clockwise direction, as shown in FIG. 21A, which in turn rotates reversing pinion 350 in the same counter clockwise direction via common drive shaft 340. As reversing pinion 350 is rotated in the counter clockwise direction, teeth of reversing pinion 350 operably engage and urge (e.g., push) teeth of upper rack 310A in direction D as shown in FIG. 21A which in turn urges distal portion 26 to deflect, bend, and/or flex in a first direction (e.g., upward). Additionally, it is understood that if movement of actuator 28 is reversed so as to move in a direction opposite of direction C, distal portion 26 will be likewise caused to deflect, bend, and/or flex in a second direction, opposite the first direction (e.g., downward).

If, however, the medical professional chooses to follow a different deflection standard, he or she may adjust the eccentric cam 370 such that eccentric cam 370 no longer urges reversing rack gear 310 downward and springs 380 return towards an uncompressed state thereby urging teeth of lower rack 310B to operably engage teeth of reversing pinion 350 while teeth of upper rack 310A are free from engagement with teeth of reversing pinion 350. In such an arrangement, movement of actuator 28 in direction C, may urge actuator rack 320 in the same direction, which in turn causes actuator pinion 330 and reversing pinion 350 to rotate in the counter clockwise direction. As reversing pinion 350 is rotated in the counter clockwise direction, teeth of reversing pinion 350 operably engage and urge (e.g., pull) teeth of lower rack 310B in direction E as shown in FIG. 21A which in turn urges distal portion 26 to deflect, bend, and/or flex in the second direction (e.g., downward). Additionally, it is understood that if movement of actuator 28 is reversed so as to move in a direction opposite of direction C, distal portion 26 will be likewise caused to deflect, bend, and/or flex in the first direction, opposite the second direction (e.g., upward). Accordingly, a medical professional may adjust the direction that distal portion 26 bends in response to actuation via actuator 28. As such, the medical professional may configure the insertion device 10 for use within either side of the patient's anatomy (e.g., within either kidney); so as to correspond to the US standard; and/or the opposite configuration, referred to as the European standard. The direction of such a reversible rack and pinion arrangements may be switched via one or more of a cam, screw, spring-loaded switch, or other appropriate component.

Insertion device 10 may further include an imaging assembly 32 shown schematically in FIG. 3. Imaging assembly 32 may include an image sensor 34 at a distal end of tubular member 20. For example, image sensor 34 may be positioned at a distalmost tip of tubular member 20. Image sensor 34 may be at least partially mounted within, or embedded within, the distal portion 26 of tubular member 20. It is also contemplated that tubular member 20 may have a distal end cap (not shown), and image sensor 34 may be positioned therein. Image sensor 34 may view an area distal to the distal end of tubular member 24.

Image sensor 34 may be any suitable type of image sensor configured to capture images and/or full-motion video images in digital or any other suitable format. Image sensor 34 may include, for example, a charged couple device ("CCD") or a complementary metal oxide semiconductor ("CMOS") image sensor. Image sensor 34 may include a pixel count greater than 20,000 pixels and less than 80,000 pixels. For example, image sensor 34 may have a pixel count of about 62,500. Image sensor 34 may include a field of view of at least 80°. For example, image sensor 34 may include a field of view of about 110-130°. In some examples, image sensor 34 may include a field of view of about 120°.

An image sensor connector 36, which may include, for example, one or more electrical wires or cables extending through an interior of tubular member 20, may connect the image sensor 34 to a printed circuit board ("PCB") 38 mounted within an interior of handle assembly 12. PCB 38 may mechanically support and/or electrically connect electronic components using conductive tracks, pads, and other features. PCB 38 may be etched from copper sheets laminated onto a non-conductive substrate. It is contemplated that electronic components like capacitors, resistors, or active devices, may be mounted on PCB 38. A signal amplifier (not shown) is one type of active device that may be mounted on PCB 38. Image data captured by image sensor 34 may be transmitted through image sensor connector 36 to PCB 38. The image data may be amplified by the signal amplifier on PCB 38. A signal converter box (not shown) is another example of an active device that may be mounted on PCB 38.

Additionally, an imaging card (not shown) may be mounted on PCB 38. The imaging card may be configured to drive the capture of image data with image sensor 34. For example, the imaging card may include appropriate circuitry and memory to calibrate captured image data from image sensor 34, deserialize the captured image data, perform known algorithms, such as demosaicing, gain control, and white balance, and/or any other suitable functions, to produce a quality color image. The gain control may be implemented by the imaging card by adjusting gains applied to the image data from image sensor 34.

Alternatively, the imaging card may include appropriate circuitry and memory to calibrate captured image data from image sensor 34, decode or deserialize the captured image data, and format the data for transmission to an external computer (not shown). The computer may perform known algorithms, such as demosaicing, gain control, and white balance, and/or any other suitable functions, to produce a quality color image. The gain control may be implemented by the computer by adjusting gains applied to the image data from image sensor 34. The imaging card may also include isolation circuitry to prevent undesired radio frequency susceptibility, emissions and interference, as well as undesired leakage currents in the event of an electrical failure. It is understood that additional or alternative devices and/or components may be mounted on PCB 38.

Insertion device 10 may also include an illumination assembly 40. As shown in FIG. 3, illumination assembly 40 may include an illumination unit 42, such as a light-emitting diode ("LED"), an illumination card or circuit board (not shown), at least one illumination fiber 44, and a heat sink (not shown). LED 42 may be mounted on PCB 38 in the interior of handle assembly 12. LED 42 may be mounted on conductive tracks or pads on PCB 38. LED 42 may emit light upon receipt of an appropriate power supply. The power supply may come from an external source such as, for example, a computer, a battery, or a power adapter, via connector 46. LED 42 may include, for example, a LUXEON Z LED. Any other suitable LED 42 may be used.

Illumination fiber 44, shown in FIG. 3, may be coupled at a proximal end to LED 42, and at a distal end to the distal end of tubular member 20. Illumination fiber 44 may transmit the light emitted by LED 42 to the distal end of tubular member 20, where the light may be emitted from the distal tip of illumination fiber 44 to areas around the distal end of tubular member 20. For example, illumination fiber 44 may direct light emitted by LED 42 towards a tissue specimen and or stone "S". Illumination fiber 44 may include an optical fiber made of plastic, glass, or any other suitable light transmissive material.

The Illumination card (not shown) may help drive and/or control operation of LED 42. For example, the illumination card may help control the light output of LED 42. It is contemplated that one or more actuators or buttons (not shown) may be disposed on handle assembly 12, for controlling operation of LED 42. Additionally or alternatively, one or more actuators or buttons may be disposed externally on a computer, for controlling operation of LED 42. In one example, gain control for imaging may be implemented by adjusting the intensity of LED 42, and adjusting the gains applied to the signals by image sensor 34. That gain control may be implemented by a computer, an imaging card, and illumination card, and/or electronic components on PCB 38.

LED 42 may generate heat when activated. The heat may be dissipated from LED 42 by one or more heat sinks (not shown). Such heat sinks may be mounted on PCB 38 using any suitable attachment. For example, a heat sink may be fastened to PCB 38 by screws and pins, and/or by fastening techniques, such as heat bonding and adhesive bonding. When mounted on PCB 38, a bottom surface of the heat sink may contact one or more surfaces of LED 42. Heat generated by LED 42 may transfer into the heat sink, and the heat sink may dissipate the heat. Heat sinks may remain out of contact with handle housing 14. This may ensure that heat dissipated from such a heat sink may not directly heat a portion of handle housing 14, thereby possibly damaging handle housing 14 or making it uncomfortable for a user to grip handle housing 14.

Referring back to FIGS. 1 and 2, handle assembly 12 may also include ports 50 and 52. Ports 50 and 52 may provide access to one or more channels (not shown) extending through tubular member 20. For example, port 52 may provide access for one or more medical devices into one or more channels extending through tubular member 20 and out the distal portion 26 of tubular member 20, as will be described in further detail below. Additionally or alternatively, port 50 may provide access into one or more working channels for delivering a suitable fluid, such as a liquid or gas, for irrigation and insufflation purposes, respectively, to and out of the distal portion 26 of tubular member 20. It is also contemplated that port 50 may be in fluid communication with one or more working channels for withdrawing material from tubular member 20 and/or an area near the distal portion 26 of tubular member 20, using suction.

As shown in FIGS. 1, 2, and 4-6, port 52 is reinforced. For example, port 52 may be reinforced with flange 54. Flange 54 may securely fix port 52 relative to handle assembly 12 so as to avoid inadvertent movement between handle assembly 12 and port 52. Accordingly, flange 54 may be configured to prevent misalignment of medical devices inserted into and through port 52 relative to handle assembly 12. Flange 54 may be coupled to handle assembly 12 and port 52 though any appropriate means. For example, flange 54 may be securely attached to handle assembly 12 and port 52 through mechanical fasteners (e.g., screws, pins, threaded connectors, etc.), adhesives, heat bonding, welding, and similar techniques. Alternatively, flange 54 may be monolithically formed with handle assembly 12 and/or port 52 such that it is a one-piece construction.

In some examples, electrical connectors such as image sensor connector 36, and/or connector 46 may extend through or alongside port 50 for coupling to an external component. In such examples, as shown in FIG. 1, port 50 may be positioned underneath handle assembly 12, while port 52 may be positioned on a top portion of handle assembly 12. For example, port 50 may be positioned at the 6 o'clock position while port 52 is positioned at the 12 o'clock position. As such, any fluid supply lines and/or electrical connectors may be out of the way of the medical professional when deploying and/or manipulating a medical device through port 52, as will be described in further detail below. In other words, because any necessary fluid supply lines and/or electrical connectors are gathered and positioned on a bottom side of handle assembly 12, the medical professional may insert and manipulate a medical device through port 52 without entangling or interfering with such fluid supply lines and/or electrical connectors.

Figure 4:
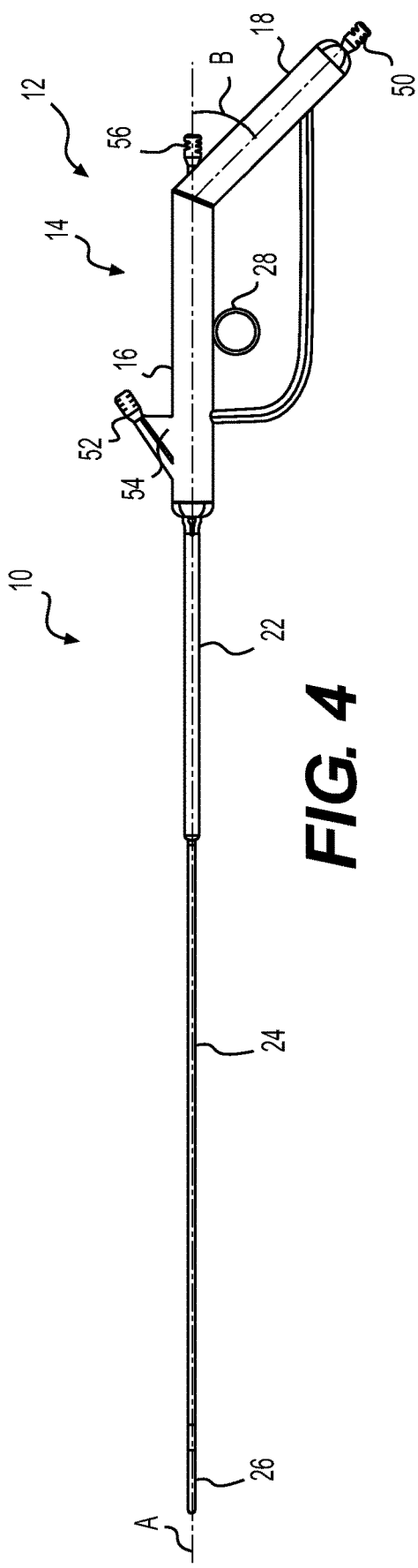
FIG. 4 depicts an insertion device according to an additional example.
Figure 5:
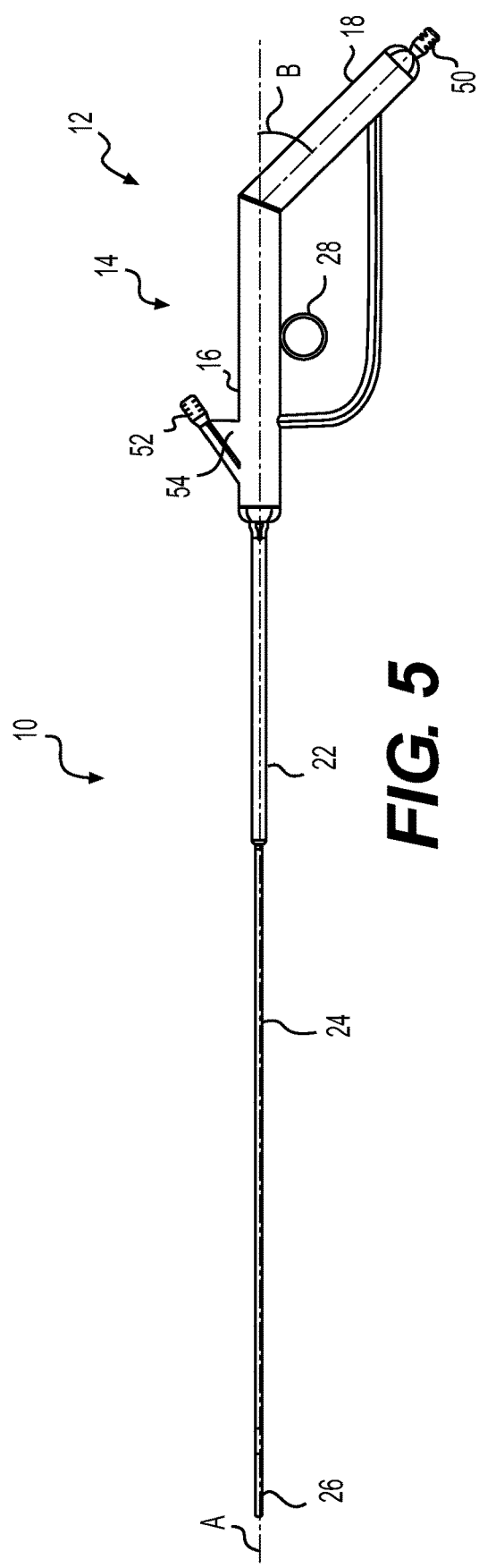
FIG. 5 depicts an insertion device according to yet another example.

In other examples, port 50 may be positioned on a proximal most portion of second portion 18 of handle housing 14 as shown in FIGS. 4 and 5. In such arrangements, any necessary fluid supply lines and/or electrical connectors are gathered and positioned away from port 52, thereby clearing space for a medical professional to insert and manipulate a medical device through port 52 without entangling or interfering with such fluid supply lines and/or electrical connectors. Additionally, as shown in FIG. 4, handle assembly 12 may include an additional port such as port 56 configured for the insertion and removal of additional or alternative tools including, for example, a lithotripter (not shown), positioned near a junction between the first portion 16 and the second portion 18 of handle housing 14 and thus, away from port 52.

Figure 6:
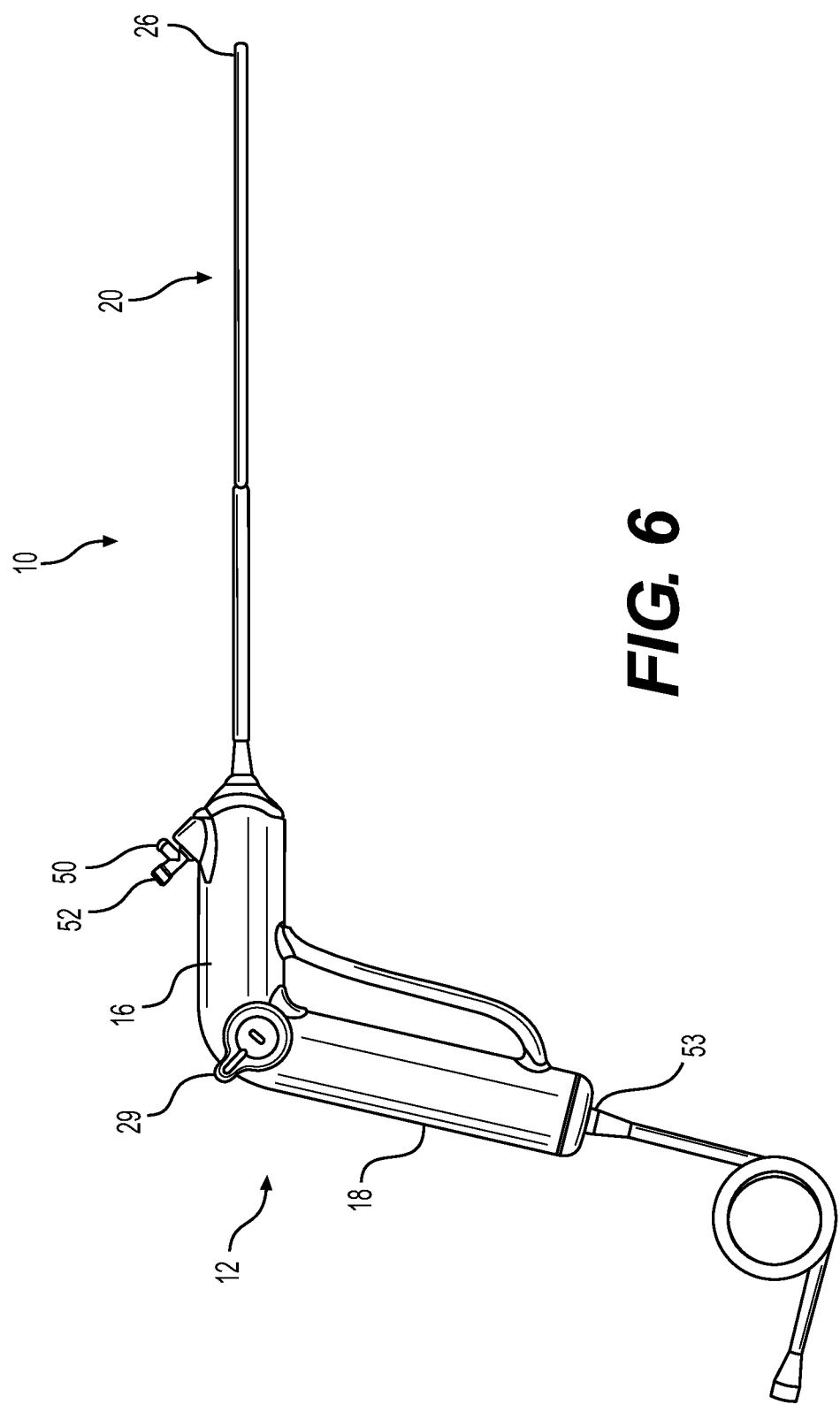
FIG. 6 depicts an insertion device according to yet another example.

In a further example, as shown in FIG. 6, handle assembly 12 may include a wheel actuator 29 for manipulating distal portion 26, rather than actuator 28. For example, wheel actuator 29 may include a wheel rotatable via a thumb or finger of the medical professional. The wheel actuator 29 may be mechanically coupled to (e.g., via a push/pull wire and/or cable) or otherwise cooperate (e.g., via an electrical servomotor) with the distal portion 26. Wheel actuator 29 may be textured and/or include one or more serrations, protrusions, and/or the like to improve a medical professional's grip on wheel actuator 29, thereby enabling improved tactile response of wheel actuator 29. Upon rotating or otherwise urging wheel actuator 29 in a first direction (e.g., clockwise), distal portion 26 may be caused to bend and/or flex in a first direction. Upon rotating or otherwise urging wheel actuator 29 in a second direction (e.g., counter clockwise), distal portion 26 may be caused to bend and/or flex in a second direction, opposite the first direction. In such a manner, distal portion 26 may be moved, angled, or otherwise manipulated in a first and a second direction within a plane so as to direct the distal portion 26 as needed during a procedure. The distal portion 26 may be operatively coupled to the wheel actuator 29 in any appropriate manner (e.g., push/pull wires, rack and pinion arrangements, reversing rack and pinion arrangements, electro-mechanical, and/or electrical components). It is understood that in some insertion device 10 orientations, actuation of wheel actuator 29 may result in less stress, strain, and/or effort imparted to or required by a medical professional actuating distal portion 26.

Additionally, as shown in FIG. 6, port 52 may provide access to one or more channels (not shown) extending through tubular member 20 to enable insertion of one or more medical devices therethrough, as discussed above. Additionally or alternatively, port 50 may provide access into one or more working channels for delivering a suitable fluid, such as a liquid or gas, for irrigation and insufflation purposes, respectively, to and out of the distal portion 26 of tubular member 20. It is also contemplated that port 50 may be in fluid communication with one or more working channels for withdrawing material from tubular member 20 and/or an area near the distal portion 26 of tubular member 20, using suction. In some arrangements, port 50 may further enable insertion of a second medical device (e.g., a laser fiber, lithotripter, etc.) therethrough. In such a manner, ports 52 and 50 may facilitate insertion of one or more medical devices and/or suitable fluids therethrough. In some arrangements, however, only a single port, e.g., port 52 may be located along the 12 o'clock position, while port 50 may either be omitted or be located at either the 6 o'clock position or along the proximal most portion of second portion 18 of handle housing 14 as shown in FIGS. 1, 4, and 5. In such a manner, any fluid supply lines and/or electrical connectors may be out of the way of the medical professional when deploying and/or manipulating a medical device through port 52.

Furthermore, a port 53 may be positioned on a proximal most portion of second portion 18 of handle housing 14 as shown in FIG. 6. Port 53 may be configured to route an integrated single cable, including electrical connectors such as image sensor connector 36, and/or connector 46 (FIG. 3), and a fluid line, for coupling to an external component including power source and fluid management system (not shown). Such an external component, having an integrated fluid management system associated therewith, may be configured to provide irrigation to distal end 26 of insertion device 10 and/or regulate fluid flow and pressure to minimize the risk of over pressurization (which may result in pyelovenous/pyelolymphatic backflow of urine and/or forniceal rupture). Such an external component may additionally include a button, knob, slide, or other such actuator (not shown) which, upon activation by the medical professional, may be caused to increase the flow (e.g., the flow rate and/or pressure) of fluid being delivered to distal end 26 of insertion device 10. Accordingly, the external component may enable "on demand" increase in fluid so as to clear a bloody, or otherwise obscured or obstructed field of view.

Figure 7:
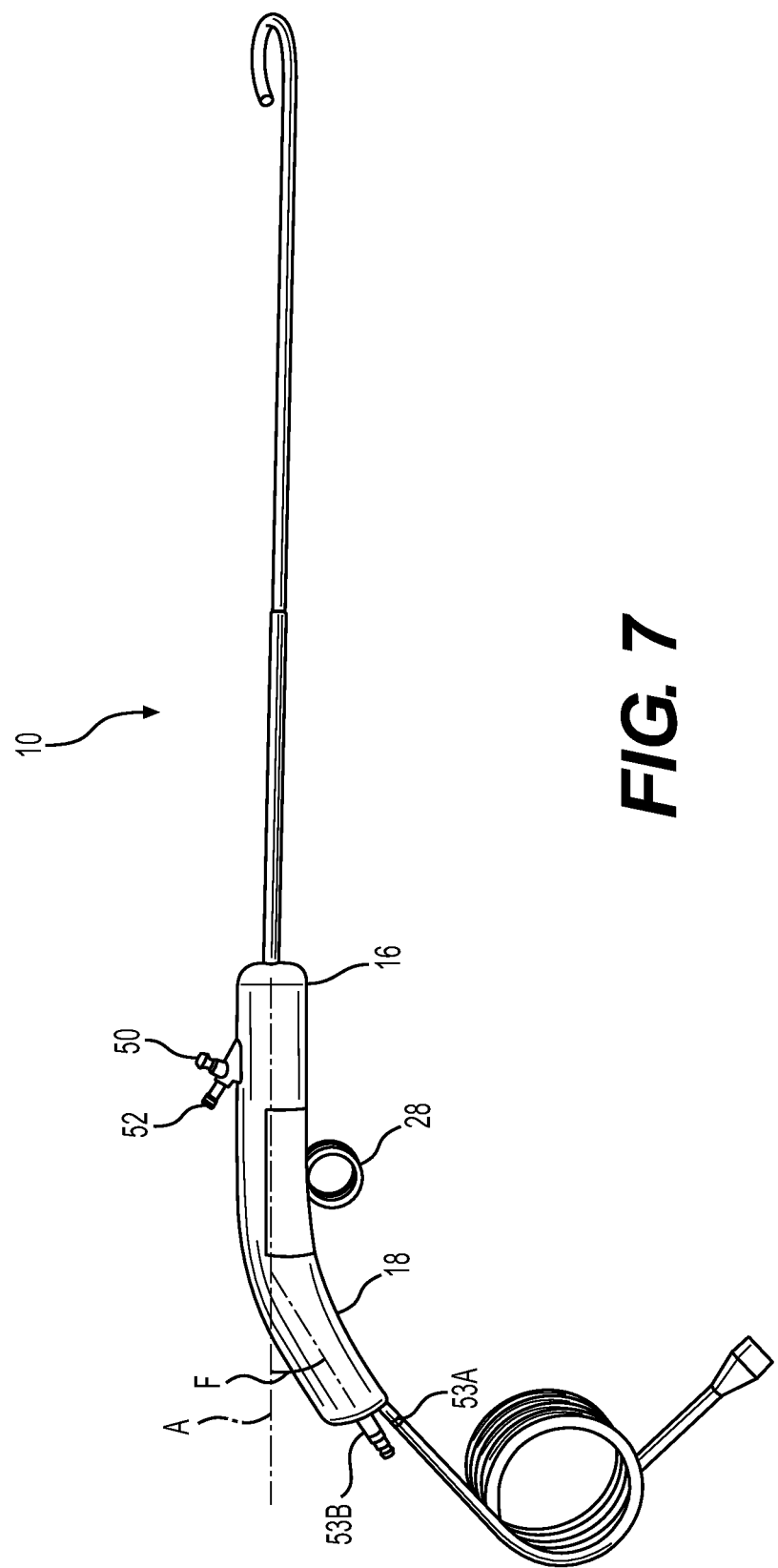
FIG. 7 depicts an insertion device according to yet another example.

In another arrangement, however, port 53 may include a first port portion 53A and a second port portion 53B, as shown in FIG. 7. For example, first port portion 53A may be configured to route electrical connectors such as image sensor connector 36 and/or connector 46 for coupling to an external component, while second port portion 53B may be configured to route any necessary fluid supply lines to the same or a different external component. That is, rather than an integrated single cable as described above in connection with FIG. 6, first port portion 53A and second port portion 53B may define separate and/or distinct ports to deliver one or more electrical connectors and/or fluid supply lines to one or more external components.

Additionally, as shown in FIG. 7, first portion 16 and second portion 18 of handle assembly 12 may be arranged such that second portion 18 is angled along a less steep or less dramatic angle, relative to the arrangement shown in FIGS. 1, 2, 4, and 5. That is, second portion 18 may extend at an angle F relative to longitudinal axis A. For example, in some examples, angle F may be about 15°. In other examples, angle B may be between about 0° and 30°, between about 10° and 25°, or between about 12° and 17°. The reduced angle F may facilitate gripping insertion device 10 along any radial orientation about longitudinal axis A, thereby enabling easier manipulation of insertion device 10 by the medical professional.

Figure 8:
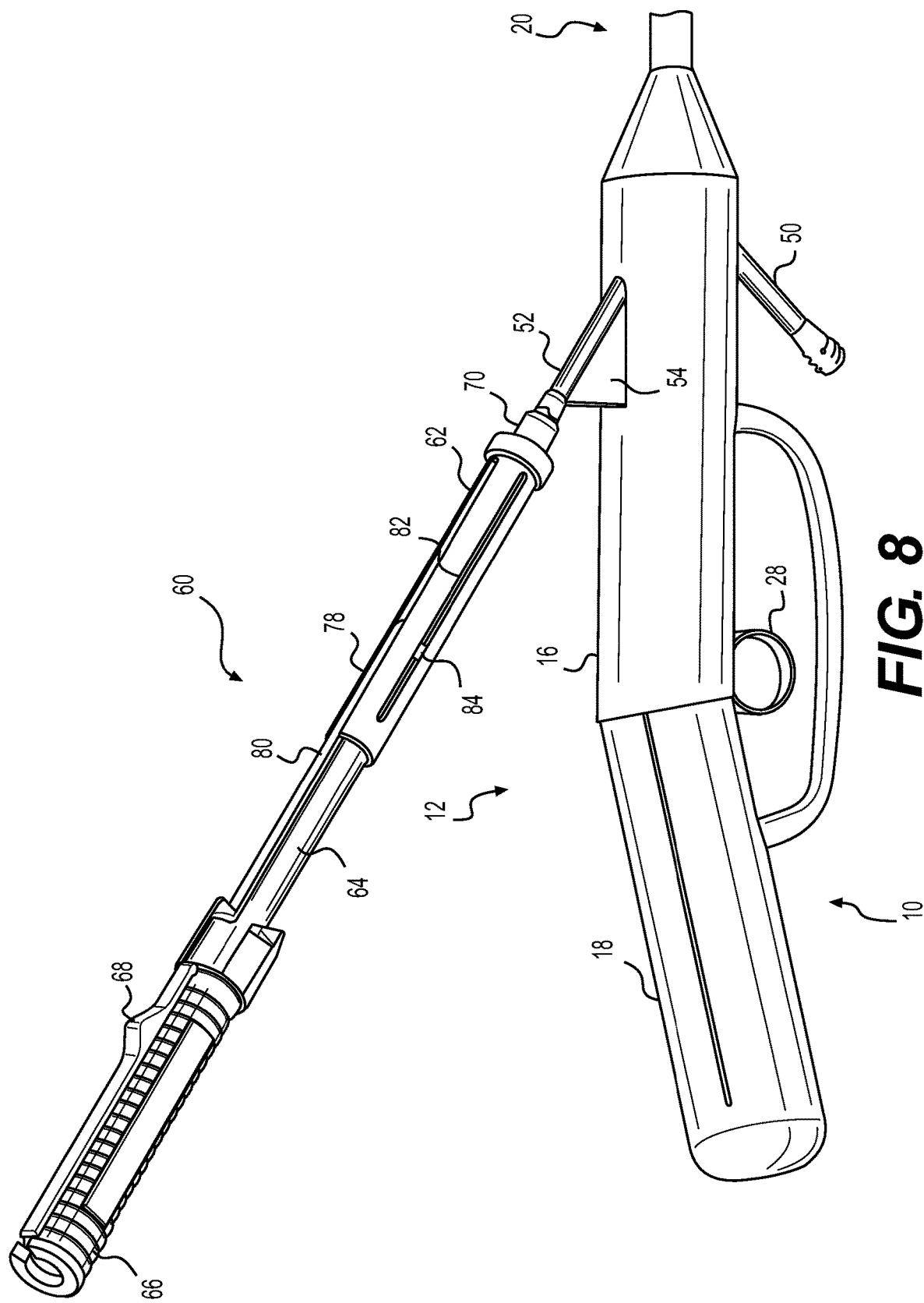
FIG. 8 depicts the insertion device of FIG. 1 coupled with an exemplary medical device handle.

As shown in FIG. 8, a medical device having a handle 60 may be coupled to insertion device 10 via port 52. For example, the medical device may include biopsy forceps, graspers, baskets, snares, probes, scissors, retrieval devices, lasers, and/or other tools. The medical device, may be routed through port 52, through a working channel of tubular member 20, and distally of distal portion 26 such that a distal portion of the medical tool may be configured to perform a procedure within the body of a patient. By way of example only, the medical device will be described in reference to a basket hereafter. It is to be understood, however, the handle 60 may be applicable to any medical device configured for insertion through a working channel of insertion device 10.

As shown in FIGS. 8 and 9, handle 60 may include a stabilizer 62, a telescopic shaft 64, a grip 66, and an actuator 68. Handle 60 may couple to port 52 via coupler 70. For example, coupler 70 may be fixedly attached or monolithically formed with stabilizer 62 and may be configured to attach over or be inserted into port 52 thereby joining handle 60 to insertion device 10. Coupler 70 may be water-tight and rotatably coupled to port 52 such that handle 60 may be rotated relative to port 52 and thereby insertion device 10. Rotation of the handle 60 may cause likewise rotation of a distal end of a medical device, thereby providing an additional degree of freedom to a medical professional during a procedure. For example, rotating handle 60 may rotate a basket, thereby allowing the medical professional to arrange or position the basket to collect a stone or other material during a procedure. The coupler 70 may be a standard luer lock screw on adapter.

Stabilizer 62, as shown in FIG. 10, may be a tubular member having an internal surface 72 with a diameter sized and configured to matingly receive telescopic shaft 64. An end 74 of stabilizer 62 opposite coupler 70 may define an opening configured to receive an end 76 (FIG. 11) of telescopic shaft 64. Additionally, stabilizer 62 may include an opening, slot, or passage 78 along an upper surface thereof. Passage 78 may be sized and configured to receive a longitudinally extending extension 80 (FIG. 11) of telescopic shaft 64. For example, extension 80 may be received within passage 78 so as to ensure proper alignment between stabilizer 62 and telescopic shaft 64. Accordingly, when assembled (FIG. 9) extension 80 resides within passage 78 to prevent inadvertent misalignment between telescopic shaft 64 and stabilizer 62. Additionally, stabilizer 62 may include a lock or similar member (not shown) configured to prevent inadvertent axial movement of telescopic shaft 64 relative to stabilizer 62. Such a lock may include a push button or similar mechanical construction which may be released by the medical professional when so desired.

In addition to passage 78, stabilizer 62 may include one or more slots 82. For example, as shown in FIG. 10, stabilizer 62 may include two slots 82 positioned on opposite sides of stabilizer 62 and approximately 90° from passage 78. In other arrangements fewer or more slots 82 may be provided through stabilizer in any appropriate arrangement. Each slot 82 may be configured to cooperate with a post, flange, or protrusion 84 of telescopic shaft 64. For example, each slot 82 may be configured to receive a corresponding protrusion 84 such that protrusion 84 may be moved along and within slot 82. In such a manner, telescopic shaft 64 may be moved axially relative to stabilizer 64, as will be described in further detail below. It is understood that in some examples, the size, shape, and/or arrangement of protrusions may be varied. For example, a first protrusion 84 may have a first shape and/or size, while a second protrusion 84 may have a second shape and/or size different from the first shape and/or size. As such, telescopic shaft 64 may be coupled to stabilizer in only a single arrangement, thereby preventing inadvertent assembly errors.

As shown in FIG. 11, telescopic shaft 64 may be coupled to grip 66. For example, telescopic shaft 64 may be secured to grip via any appropriate mechanical fastener (e.g., screws, pins, and/or threaded connectors) or coupling techniques such as, for example, welding, heat bonding, and/or adhesives. Alternatively, grip 66 may be monolithically formed with telescopic shaft 64 such that telescopic shaft 64 and grip 66 are a one-piece construction. For example, telescopic shaft 64 and grip 66 may be extruded as a one-piece construction.

Telescopic shaft 64 may be a hollow generally U-shaped member having one or more flex arms 86. For example, as shown in FIG. 11, each flex arm 86 may include a narrow or thin cantilevered member including at least one protrusion 84 thereon. As shown, a width $W_1$ of each flex arm 86 may be smaller than a width $W_2$ of surrounding portions of telescopic shaft 64. Accordingly, each flex arm 86 is more flexible than surrounding portions of telescopic shaft 64. As such, each flex arm 86 may bend and its associated protrusion 84 may be received within a corresponding slot 82 on stabilizer 62 in a snap-fit arrangement. Once positioned within a slot 82, each protrusion 84 may move along and within track 82 as will be described in further detail below.

Grip 66 may include one or more baffles 88 configured to aid a medical professional with securely grasping grip 66. Any number and arrangement of baffles 88 may be disposed on grip 66. Additionally, grip 66 may include a slide recess 90 as shown in FIG. 11. Slide recess 90 may be a longitudinally extending opening extending through grip 66 and configured to matingly receive actuator 68 moveably therein. For example, actuator 68, as shown in FIG. 12, may include a thumb or finger rest 92 and arms 94. In use, a medical professional may urge rest 92 distally along slide recess 90 so as to actuate the medical device (e.g., open a basket). As such, a distal end 98 of actuator 68 may be coupled to the medical device such that movement of the actuator 68 causes likewise movement of the medical device. For example, the medical device may include a sheath (not shown) and drive wire (not shown) including a distal assembly (e.g., basket) (not shown) on a distal end thereof. The distal end 98 of actuator 68 may be fixedly coupled to the drive wire while the sheath may be fixedly coupled to telescopic shaft 64. Accordingly, distal movement of actuator 68 may urge the drive wire and distal assembly of the medical device relative to the sheath of the medical device, thereby expanding or opening the distal assembly of the medical device. Arms 94 may be configured to be matingly cooperate with and be received within an opening 96 of grip 66 as shown in FIG. 9. For example, an external surface of each arm 94 may be configured to slide along an internal surface of opening 96. As such, arms 94 maintain actuator 68 within grip 66 and while allowing relative movement between actuator 68 and grip 66 so as to actuate the medical device. It is understood that other arrangements of arms 94 may be used such as, for example, a single semi-circular arm or other configuration may be used without departing from the scope of this disclosure.

While FIGS. 8, 9, and 12 depict a longitudinally slideable actuator 68, it is understood that additional or alternative actuation mechanisms may be used without departing from the scope of this disclosure. For example, a roller wheel 100 (FIG. 13) and/or a toggle lever 102 (FIG. 14) may be used so as to actuate the medical device (e.g., open a basket). As such, actuator 100 or 102 may be coupled to the medical device such that movement of the actuator 100 or 102 causes likewise movement of the medical device. For example, the medical device may include a sheath (not shown) and drive wire (not shown) including a distal assembly (e.g., basket) (not shown) on a distal end thereof. The actuator 100 or 102 may be fixedly coupled to the drive wire while the sheath may be fixedly coupled to telescopic shaft 64. Accordingly, movement of actuator 100 or 102 may urge the drive wire and distal assembly of the medical device relative to the sheath of the medical device, thereby expanding or opening the distal assembly of the medical device.

Figure 15:
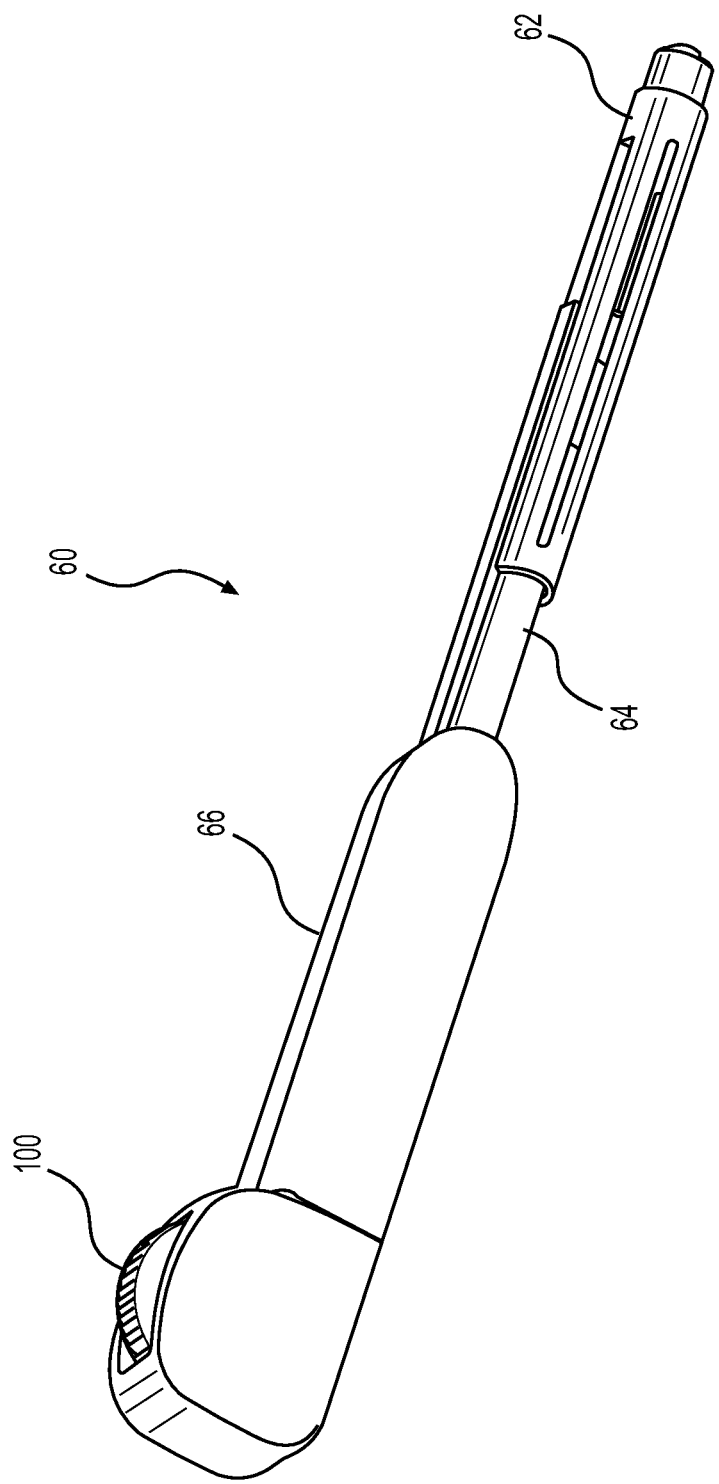
FIG. 15 depicts a further exemplary actuator of a medical device handle.
Figure 16:
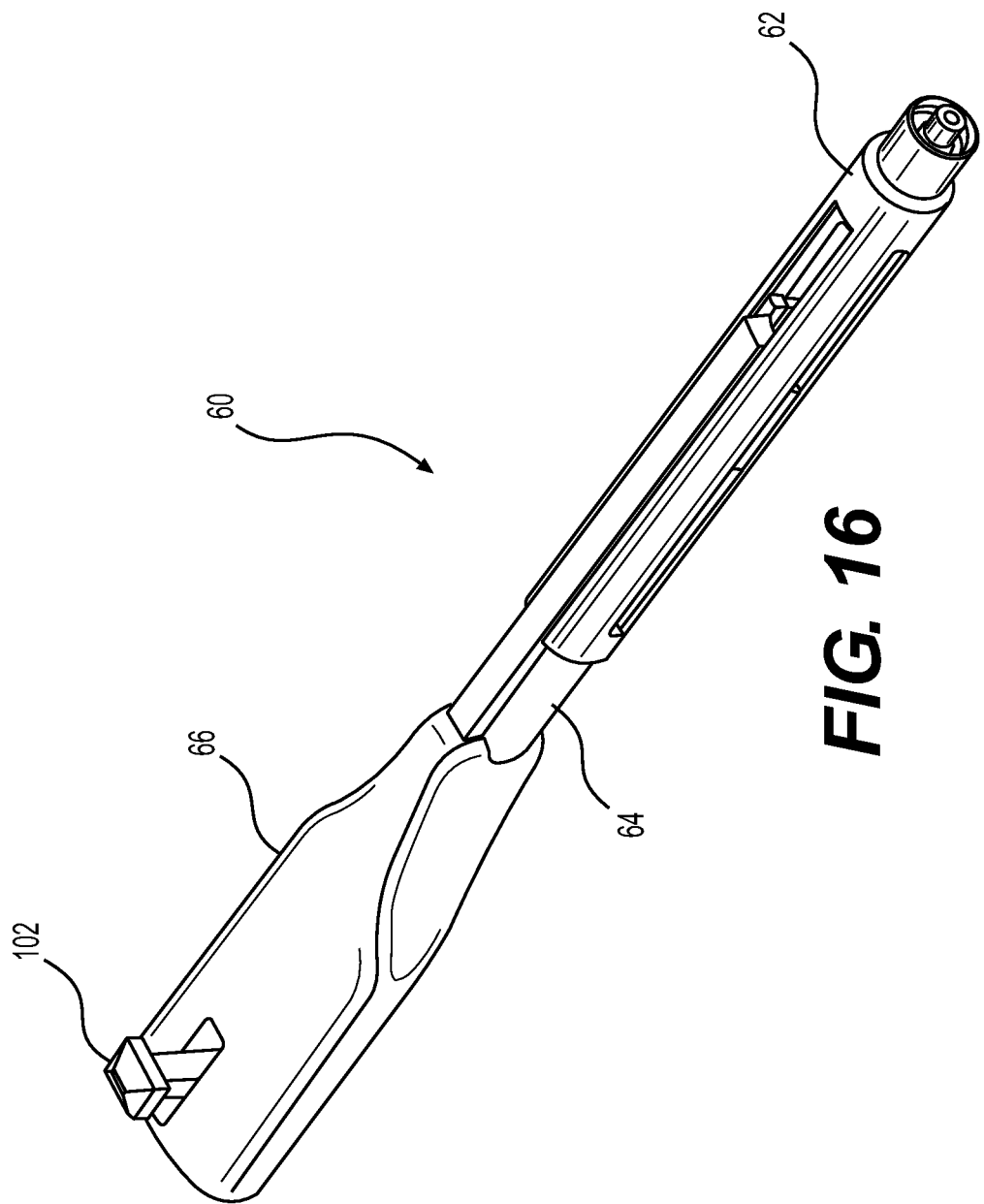
FIG. 16 depicts an additional exemplary actuator of a medical device.

As noted above, FIG. 13 and FIG. 14 illustrate a roller wheel 100 and a toggle lever 102, respectively, along a distal portion of grip 66. However, the disclosure is not so limited. For example, roller wheel 100 and toggle lever 102 may each be positioned along a proximal end of grip 66, as shown in FIGS. 15 and 16, respectively. In such an arrangement, each of handles 60 of FIGS. 15 and 16 may also be readily used with conventional insertion devices such as, for example, flexible endoscopes, flexible cystoscopes, flexible gastroscopes, flexible duodenoscopes such as Boston Scientific Spyglass II, flexible colonoscopes, or other flexible scopes used in medicine and other fields, without inducing additional ergonomic strain. For example, as discussed above, flexible scopes are designed to be held in the vertical or upright position which necessitates that the medical professional tightly flex his or her arm at the elbow to bring their forearm parallel to their body and bend their wrist outward to grasp the conventional insertion device with his or her dominate hand. Placement of roller wheel 100 and/or toggle lever 102 along the proximal end of grip 66 enables the medical professional to orient his non-dominate hand and arm in a similar fashion as the upright dominate arm and hand to hold handle 60. That is, both arms of a medical professional may be aligned in a general parallel orientation so as to accommodate ergonomic and anatomic considerations.

Figure 17A:
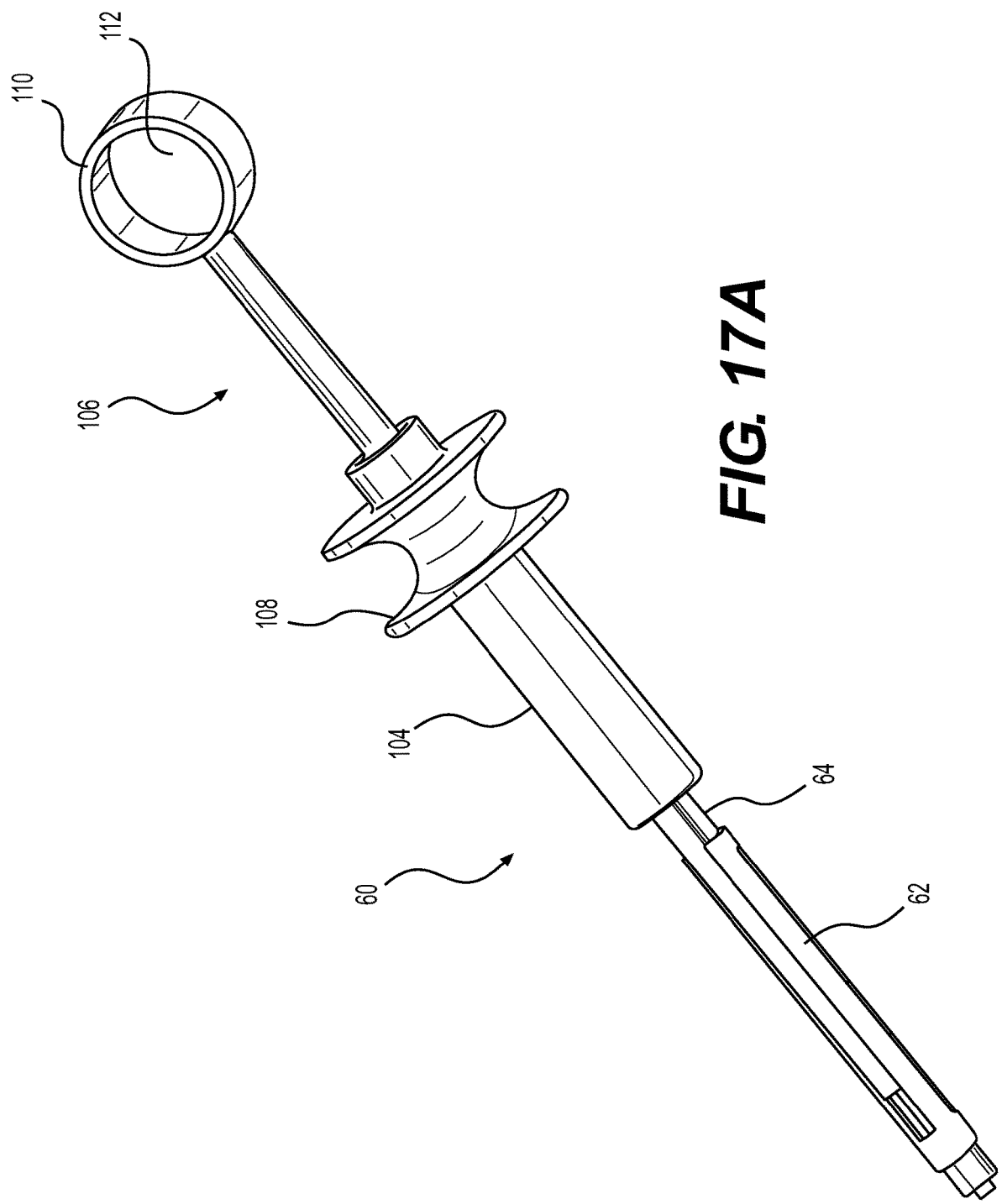
Figure 17B:
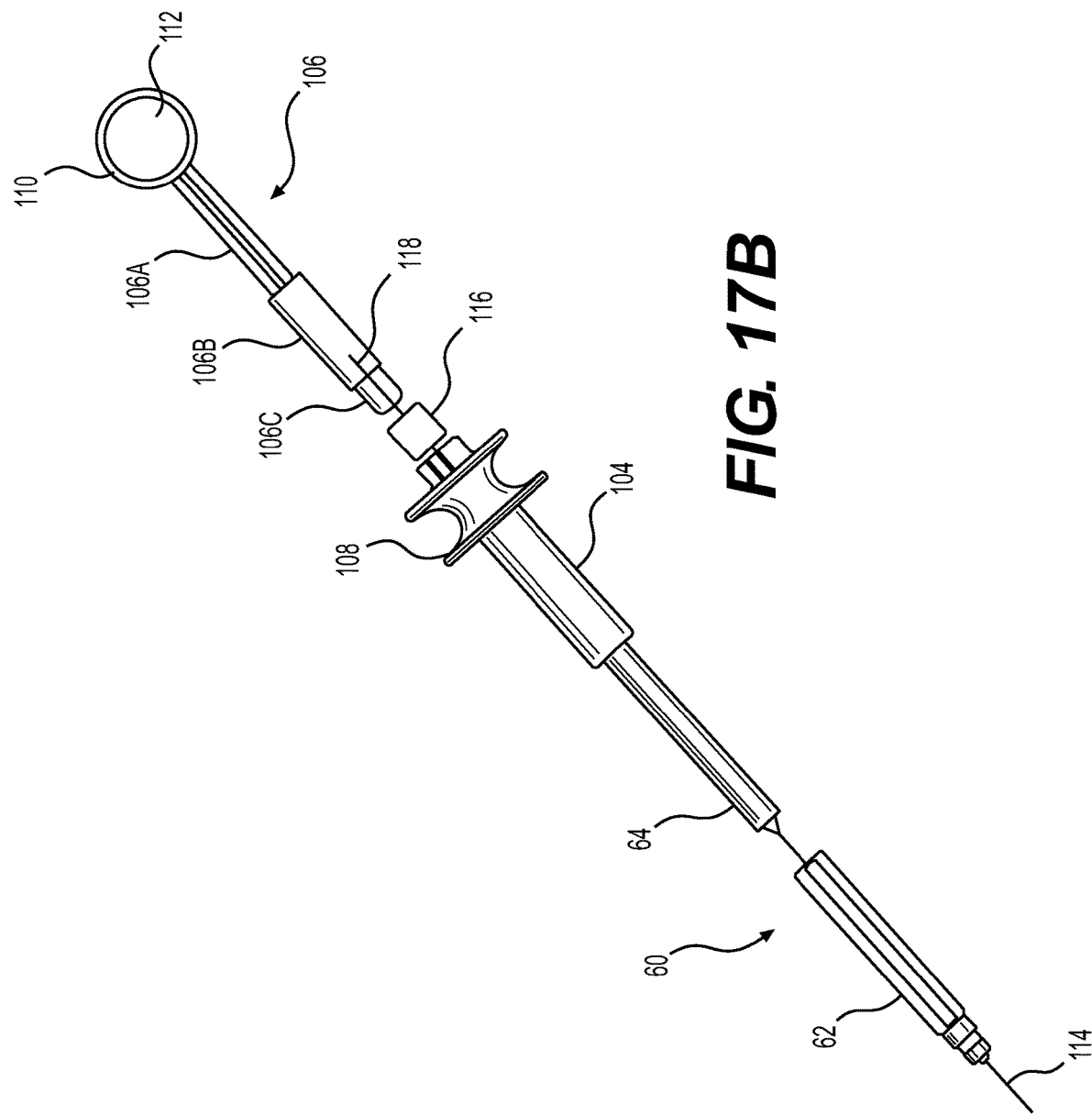

FIGS. 17A-17C illustrate another exemplary actuator of a medical device handle 60 having a syringe configuration. Similar to handle 60 described above in connection with FIG. 8, handle 60 of the example shown in FIG. 17A includes a stabilizer 62 and a telescopic shaft 64. Rather than grip 66 and actuator 68, however, handle 60 of FIG. 17A includes a tube 104 including a finger grip 108. As shown, tube 104 may be configured to receive a plunger 106, defining a thumb or finger ring 110, movably therein. That is, plunger 106 may be axially translatable within tube 104. For example, ring 110 may include a loop and/or a circular hole or opening 112, through which a thumb or finger of a medical professional may be inserted. Upon urging ring 110 distally, an end-effector assembly (e.g., basket) of the medical device may extend distally of a sheath (not shown) of the medical device. Once distal of the sheath, the end-effector assembly may radially expand to open.

FIG. 17B illustrates an exploded view of the handle 60 of FIG. 17A. As shown, plunger 106 may have a varied cross-section. That is, a first portion 106A of plunger 106 may have a first cross-sectional shape (e.g., cross or x-shape), a second portion 106B may have a generally circular cross-sectional shape, and a third portion 106C may have a generally circular cross-sectional shape having a smaller diameter than the second portion 106B. As shown, an end-effector assembly (e.g., basket) of the medical device may be coupled to plunger 106 via an elongate wire, shaft, tube, or other such member, 114. Wire 114 may extend proximally from the end effector (not shown) through and/or along stabilizer 62, through and/or along telescopic shaft 64, through and/or along tube 104, through and/or along a lock or vise 116, into plunger 106 and through a slit or hole 118 extending along at least a portion (e.g., second portion 106B and third portion 106C) of plunger 106. That is, a proximal end of wire 114 may be passed from a location within plunger 106, and through slit 118. To secure wire 114 (and the end effector of the medical device) relative to plunger 106, vise 116 may be rotatably coupled, moved over, positioned about, or otherwise arranged along third portion 106C. As such, vise 116 may compress third portion 106C and slit 118 so as to pinch or otherwise retain wire 114 relative to plunger 106. Further, the sheath (not shown) of the medical device may be fixedly coupled to telescopic shaft 64. In such a manner, axial translation of plunger 106 relative to tube 104 may result in axial displacement of the end effector of the medical device, relative to the sheath (not shown) of the medical device, thereby enabling the end effector to deploy and/or expand.

In order to prevent the medical professional from inadvertently pulling plunger 106 out of tube 104, a proximal end of shaft may include one or more detents 120, as shown in FIG. 17C. Detents 120 may define a flange or abutment surface 122 which may limit proximal retraction of plunger 106 once inserted within tube 104. That is, detents 120 may flex radially outwardly from a central longitudinal axis of tube 104 such that plunger 106 and vise 116 may be inserted therein. However, abutment surface 122 of detents 120 may cooperate with a proximal end of second portion 106B of plunger 106 to limit or interfere with proximal retraction thereof. In such a manner, plunger 106 may be retrained with tube 104. In other arrangements, however, tube 104 may not include detents 120. Rather, after insertion of plunger 106 within tube 104, a cap (not shown) may be coupled (e.g., screwed) onto a proximal end of tube 104. In such a manner, plunger 106 and tube 104 may be selectively uncoupled from one another to enable cleaning, repair, or when necessary to address an oversized stone or other material.

Figure 18:
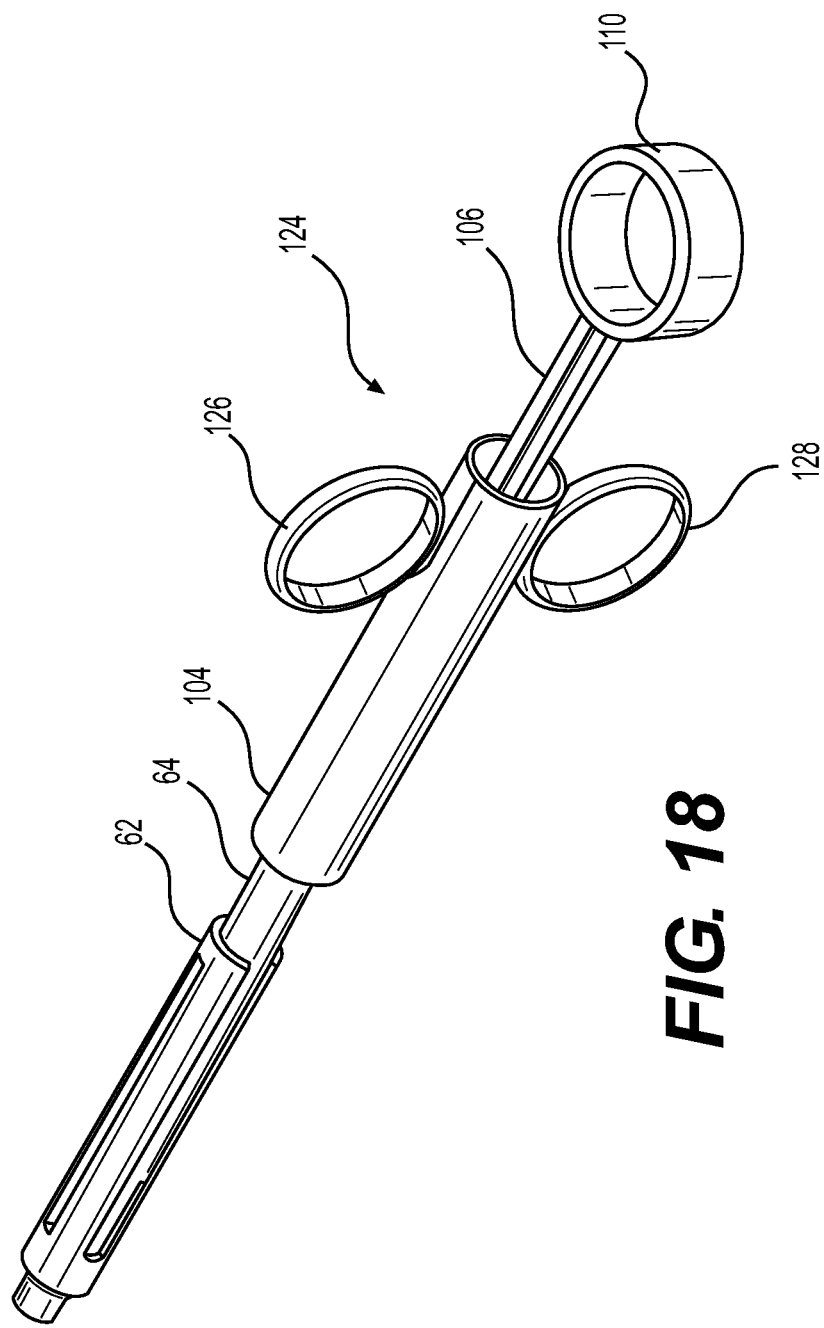
FIG. 18 illustrates a further exemplary actuator of a medical device handle.
Figure 19:
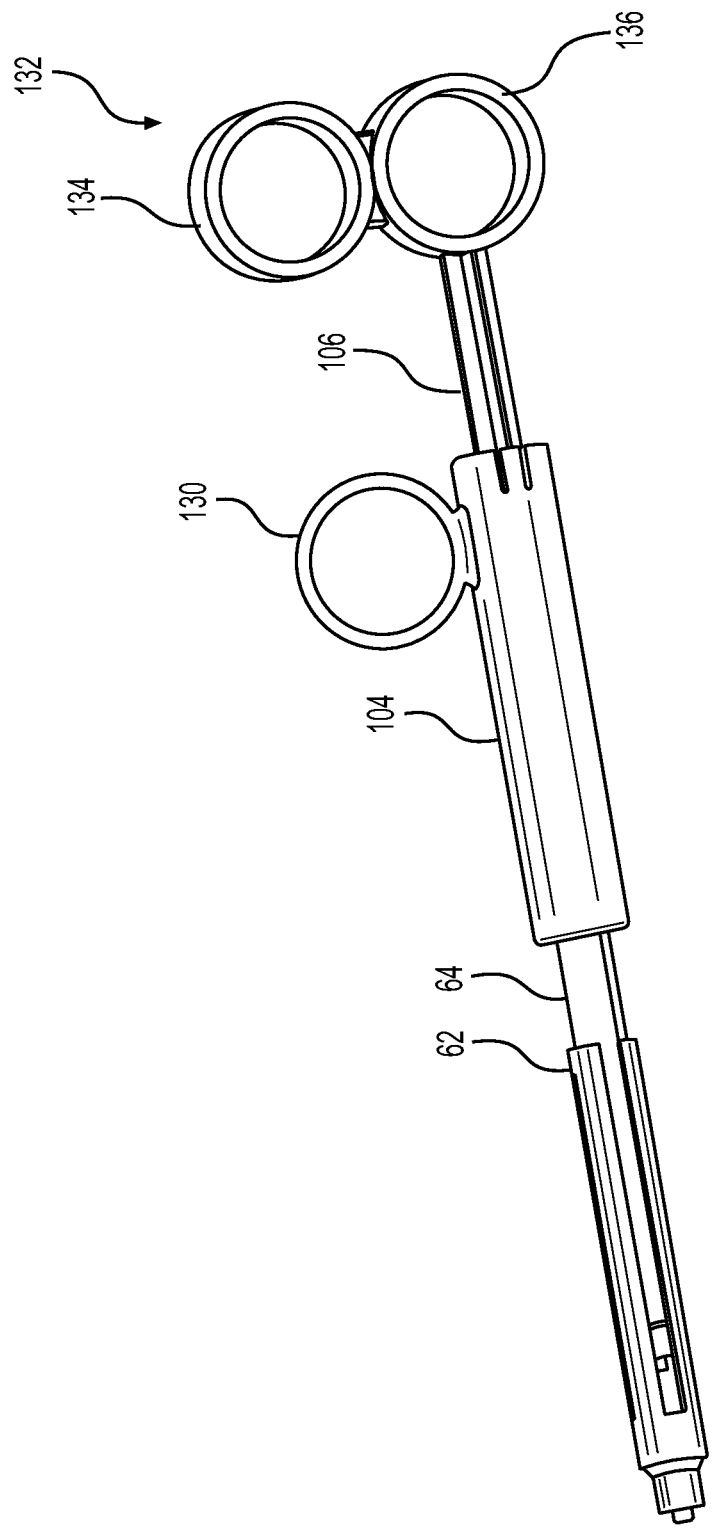
FIG. 19 illustrates an additional exemplary actuator of a medical device.

Alternative arrangements of finger grip 108 are also contemplated. For example, as shown in FIG. 18, finger grip 108 may be replaced by a double finger ring 124 arrangement. That is, a first finger ring 126 and a second finger ring 128 may be symmetrically arranged along tube 104. Accordingly, the medical professional may place each of his or her index and middle fingers through one of the first and second finger rings 126 and 128, and his or her thumb or another finger through the finger ring 110. In so doing, a medical professional may manipulate his or her hand so as to advance and retract double finger ring 124 arrangement, and therefore tube 104, relative to finger ring 110, and therefore plunger 106 so as to advance and retract the end effector of a medical device. Further, in another example, as shown in FIG. 19, an alternative arrangement may include a single finger ring 130 coupled to tube 104 while a double finger ring 130 arrangement, including first and second finger rings 134 and 136, may be coupled to plunger 106. That is, plunger 106 may be coupled to second finger ring 136 which may be in turn coupled to a first finger ring 134. Accordingly, the medical professional may place each of his or her index and middle fingers through one of the first and second finger rings 134 and 136, and his or her thumb or another finger through the finger ring 130. In so doing, a medical professional may manipulate his or her hand so as to advance and retract double finger ring 132 arrangement, and therefore plunger 106, relative to finger ring 130, and therefore plunger tube 104 so as to advance and retract the end effector of a medical device.

Figure 22B:
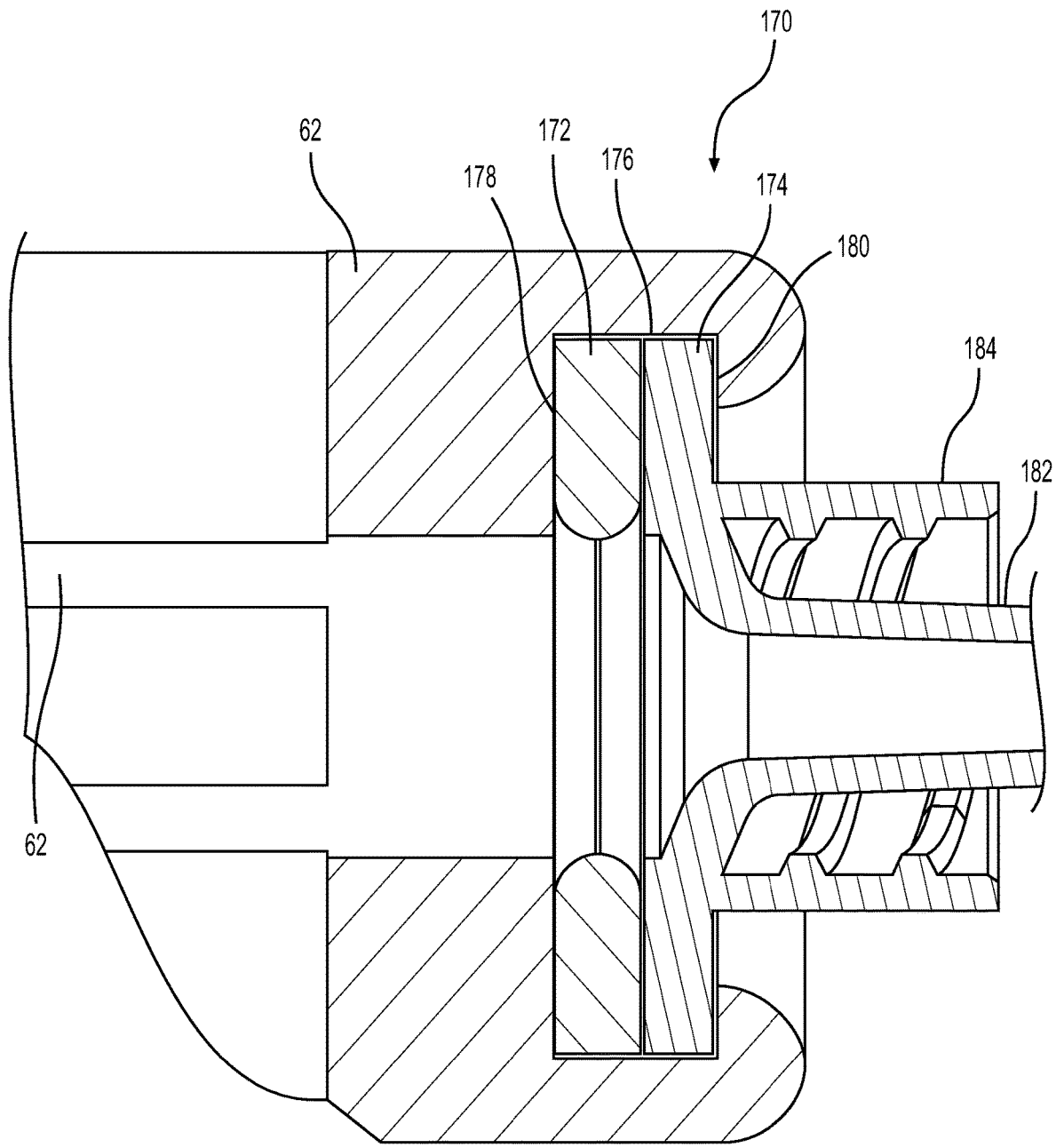

As noted above, and as shown in FIGS. 8 and 9, handle 60 may couple to port 52 of insertion device 10 via coupler 70. Additionally, however, any of the above disclosed medical device handles 60 may include coupler 70 coupling telescopic shaft 64 and grip 66. In either arrangement, such couplers 70 may be rotatable and water tight. Further, an exemplary coupler 170 may be constructed as shown in FIGS. 22A and 22B. For example, as shown in FIGS. 22A and 22B, coupler 170 may include a gasket such as, for example, an O-ring 172. O-ring 172 may enable a water tight seal in medical device handle 60. Additionally, coupler 170 may include a rotatable male luer lock fitting 174 configured for coupling with a correspondingly shaped female luer lock fitting (not shown). That is, as shown in FIG. 22B, for example, male luer lock fitting 174, along with O-ring 172, may be positioned, received, and/or retained within a portion of stabilizer 62. For example, stabilizer 62 may define a pocket 176, recesses, groove, or other such structure configured to receive O-ring 172 and male luer lock fitting 174 therein. As shown, pocket 176 may include a first surface 178 and a second surface 180 extending along a longitudinal axis of stabilizer 62. First and second surfaces 178 and 180 may be spaced longitudinally so as to limit sliding of O-ring 172 and male luer lock fitting 174 along the longitudinal axis of stabilizer 62, while still enabling sufficient space to allow male luer lock fitting 174 to freely rotate therein. As shown, male luer lock fitting 174 may have an inner coupling port 182 and an outer internally threaded extension 184. A female luer lock fitting (not shown) may be coupled to male luer lock fitting 174 between coupling port 182 and extension 184, as is known in the art. Accordingly, coupling 170 may enable a water tight rotatable connection between two components, such as, for example, between stabilizer 62 and port 52 (or any other such port), and/or between telescopic shaft 64 and grip 66.

Figure 20:
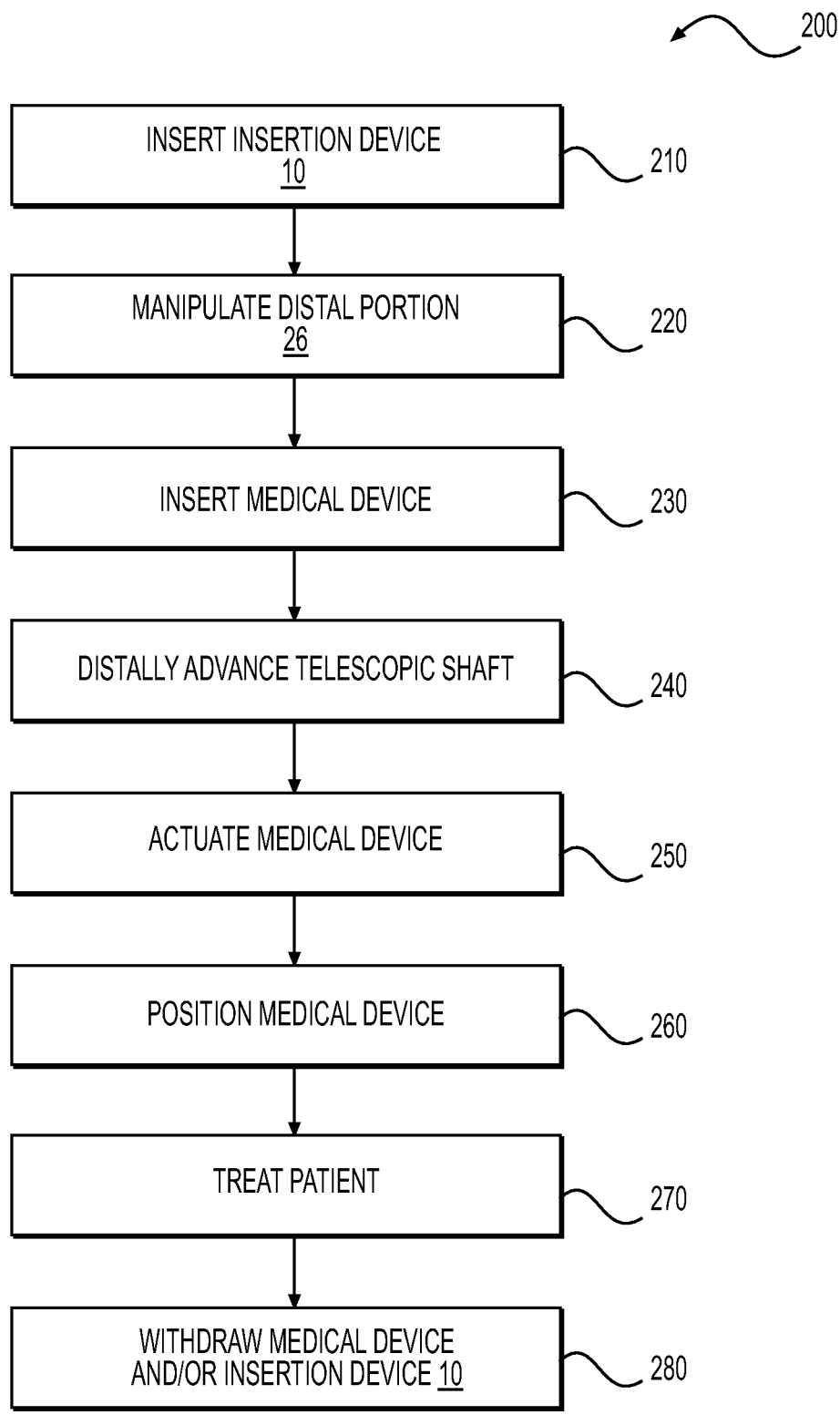
FIG. 20 depicts an exemplary method of use of the insertion devices of FIGS. 1-7 and the medical device handles of FIGS. 8-19.

An exemplary method 200 of use will now be described with reference to FIG. 20. First, a medical professional may insert the insertion device 10 into the body of a patient at step 210. For example, a distal end of the insertion device 10 may be inserted through the urethral meatus of the ureter. Once inserted, the medical professional may optionally deflect the distal portion 26 of insertion device 10 as necessary to direct the distal portion 26 towards an area or object of interest within the body of the patient as shown at step 220. As such, the medical professional may rotate the insertion device 10 through a desired angular range of motion and/or manipulate actuator 28 to bend, deflect, or otherwise move distal portion 26 as desired. A medical professional may gauge the proper placement of the distal portion 26 of the medical device under the guide of the imaging 32 and illumination 40 assemblies described above (FIG. 3).

If the medical professional determines there is a need for the insertion of a medical device, he or she may insert said device through port 52 as step 230. For example, the medical professional may use one hand, for example, the dominant hand, to maintain a grasp on the insertion device while using his or her second hand, for example, the non-dominant hand, to position a medical device, for example, a basket, through the port 52. As such, the medical professional may attach coupler 70 to port 52, thereby coupling the handle 60 of the medical device and stabilizer 62 to insertion device 10. It is understood that in some examples, stabilizer 62 and the medical device may be coupled to port 52 prior to insertion of the insertion device 10 into the body of the patient.

As noted above, stabilizer 62 may include a lock configured to prevent accidental axial movement of telescopic shaft 64 relative to stabilizer 62. Accordingly, when the medical professional determines the need to deploy the medical device, for example, a basket, he or she may unlock the stabilizer and allow telescopic shaft 64 to move relative to stabilizer 62 at step 240. For example, unlocking stabilizer 62 may allow telescope shaft 64 to move distally relative to and within stabilizer 62 such that a distal portion of the basket may extend distally of distal portion 26 of insertion device 10.

Once the distal portion of the medical device, e.g., basket, is extended distally of distal portion 26, a medical professional may actuate the basket to open so as to be configured to receive an object therein at step 250. To do so, the medical professional may urge any one or more of actuator 68, 100, 102, and 110 to cause an end-effector assembly of the basket to extend distally of a sheath (not shown) of the basket. Once distal of the sheath, the end-effector unit may radially expand to open and receive a stone or other material therein. If the medical professional needs to redirect or aim the basket to a different orientation, he or she may rotate the handle 60, and thereby end-effector so as to re-orient the end-effector as needed at step 260. Once at the desired position, the medical professional may treat the patient with the medical device by, for example, capturing a stone or other material within the basket at step 270. Once a desired treatment is completed, a medical professional may withdraw or remove the medical device and/or insertion device 10 at step 280.

The insertion device 10 and medical device handle 60 of the instant disclosure provide numerous features. For example, the insertion device 10 and handle 60 of the medical device may be operated by the dominant and non-dominant hand, or vice versa, respectively, of a single medical professional. Accordingly, the need for precise communication between the medical professional and any assistants is reduced as the entire procedure may be performed by a single operator. Indeed, as the dominant hand, for example, may remain on the insertion device 10 throughout operation, the medical professional may maintain all three degrees of freedom of the insertion device. First, the medical professional may ensure x-axis depth control of the tubular member 20 of the insertion device 10 within the body of the patient. Due to the rigid and semi-rigid nature of the proximal portion 22 and medial portion 24, respectively, the need for the medical professional to hold the insertion device with his/her non-dominant hand at the urethral meatus to control insertion depth is eliminated. Rather, the robust (e.g., thick) nature of these portions prevent egress of the tubular member 20 back out of the urethra of a patient. Second, the medical professional may use a finger or thumb of the dominant hand to push and/or pull actuator 28 to control bending or deflection of the distal portion 28 within the y-axis. Additionally, the medical professional may rotate the insertion device 10 with his or her dominant hand thereby enabling full z-axis control of insertion device 10. Accordingly, the medical professional is provided with a full range of motion of the insertion device 10 with only a single hand, thereby freeing his or her other hand for manipulation of a medical device. Additionally, the time necessitated by a medical procedure may be reduced since time spent advising and/or instructing an assistant may be reduced.

Further, since a medical professional is able to hold the angled configuration of the handle assembly 12 in line with their forearm in a natural position (e.g., across their waist), the handle assembly 12 decreases carpal tunnel strain. Additionally, the pistol-like grip of handle assembly 12 enables an ergonomic grasping of insertion device 10 making manipulation of the insertion device increasingly comfortable and user-friendly by keeping the medical professional's wrist in line with longitudinal axis A of insertion device 10 during rotation and other manipulation of insertion device 10. The angled or pistol-like grip of handle assembly 12 additionally enables greater rotational freedom along longitudinal axis A as a medical professional can generally rotate his or her arm through a larger range of motion when held in the natural position with their wrist in line with longitudinal axis A rather than held upright with their wrist sharply bent with respect to longitudinal axis A. Further, the angled or pistol-like grip of the handle assembly 12 may be universally grasped by the medical professional's hand, whether or not they are right-handed or left-handed, thus removing the need for specialized instruments for different medical professionals. Finally, since the insertion device 10 is configured (e.g., via pistol-like grip of handle assembly 12) to be held in the natural position with their wrist in line with longitudinal axis A, the movement of the distal portion 26 may be made more intuitive than conventional insertion devices by mimicking the pointing and flexing of the medical professional's index finger.

Further, the semi-rigid construction of tubular member 20 provides a number of additional advantages. Beyond facilitating single hand control by the medical professional, the tubular member 20 may be greatly reduced in overall length compared to conventional insertion devices. As such, the overall cost of goods required for manufacture may be reduced. Decreased overall length also enables improved rotational responsiveness of a medical device extending through the tubular member 20 and less binding or kinking of the medical device since the tubular member 20 extends substantially straight along the longitudinal axis A. Additionally, positioning of the port 50, and the optional port 56, away from port 52 may clear space for a medical professional to insert and manipulate a medical device through port 52 without entangling or interfering with fluid supply lines, electrical connectors, and/or additional tools.

Additionally, the handle 60 enables a medical professional to control manipulation of the medical device with a single hand, for example, the non-dominant hand. Indeed, the inclusion of stabilizer 62 allows a medical professional to quickly and easily control the depth of insertion of the medical device. Additionally, the medical device may be quickly and easily actuated via actuator 68 and rotation of handle 60 such that a single medical professional may operate the medical device. Accordingly, the described insertion device 10 and medical device handle 60 provide a medical professional command and control of the aspects of the medical system throughout a procedure thus enhancing procedure efficiency and reducing the number of hands/people required for completion of the procedure. Additionally, it is understood that the disclosed medical device handle 60 may be used in conjunction with any scope and/or insertion device readily available. For example, medical device handle 60 may be used with a conventional scope and/or insertion device, such as any flexible, semi-rigid, and/or rigid insertion device.

It is to be understood that any of the various insertion device 10 arrangements described herein may be used with any of the described medical device handles 60 described herein. Additionally or alternatively, any of the described insertion devices 10 may include any of the described actuator 28, wheel actuator 29, or other such actuators configured to deflect distal portion 26. More so, any of the described insertion device 10 may include any of ports 50, 52, 53, and/or first and second port portions 53A and 53B, in any location along insertion device 10 so as to facilitate insertion and retraction of one or more medical devices, and/or routing any necessary fluid supply lines, electrical connectors, and/or integrated fluid and electrical supply lines.

While principles of the present disclosure are described herein with reference to illustrative examples for particular applications, it should be understood that the disclosure is not limited thereto. Those having ordinary skill in the art and access to the teachings provided herein will recognize additional modifications, applications, examples, and substitution of equivalents all fall within the scope of the examples described herein. Accordingly, the disclosure is not to be considered as limited by the foregoing description.

I claim:
1. A medical device, comprising:
a C-shaped stabilizer defining a longitudinally extending passage and configured to be coupled to a port of an insertion device;
a shaft configured for telescopic translation within the stabilizer, wherein the shaft includes at least one extension movably received within the passage;
a grip coupled to the shaft; and
an actuator coupled to the grip, wherein the actuator is axially moveable relative to the grip so as to selectively actuate a distal assembly of the medical device,
wherein the stabilizer further includes a first longitudinally extending slot on a first side of the passage, and a second longitudinally extending slot on a second side of the passage opposite the first side, and wherein a length of the first longitudinally extending slot or the second longitudinally extending slot is less than a length of the longitudinally extending passage.

2. The medical device of claim 1, wherein the shaft includes a pair of protrusions extending radially outwardly from a sidewall thereof, wherein each of the pair of protrusions is positioned to be received within a respective one of the first longitudinally extending slot or the second longitudinally extending slot.

3. The medical device of claim 1, wherein the shaft is coupled to the stabilizer in a snap-fit arrangement.

4. The medical device of claim 1, wherein the stabilizer is configured to be rotatably coupled to an insertion device.

5. The medical device of claim 1, wherein the actuator includes at least one arm, wherein the arm has an external surface configured to matingly cooperate with an internal surface of the grip.

6. The medical device of claim 5, wherein the actuator includes at least two arms, wherein each of the at least two arms has an external surface configured to matingly cooperate with an internal surface of the grip.

7. The medical device of claim 6, wherein the at least two arms of the actuator form a C-shaped extension.

8. The medical device of claim 1, wherein the stabilizer includes a coupler monolithically formed therewith.

9. The medical device of claim 1, wherein a distalmost end of the grip is proximal of a proximalmost end of the stabilizer.

10. A medical device, comprising:
    a stabilizer configured to be coupled to a port of an insertion device;
    a shaft configured for telescopic translation within the stabilizer, wherein the shaft includes a pair of flex arms and a pair of protrusions, wherein a first protrusion of the pair of protrusions is positioned on a first flex arm of the pair of flex arms, and wherein a second protrusion of the pair of protrusions is positioned on a second flex arm of the pair of flex arms;
    a grip coupled to the shaft; and
    an actuator coupled to the grip, wherein the actuator is axially moveable relative to the grip so as to selectively actuate a distal assembly of the medical device.

11. The medical device of claim 10, wherein the shaft further includes a longitudinally extending extension positioned within a longitudinally extending opening of the stabilizer.

12. The medical device of claim 10, wherein the stabilizer is C-shaped.

13. The medical device of claim 10, wherein the actuator includes at least one arm, wherein the at least one arm has an external surface configured to matingly cooperate with an internal surface of the grip.

14. The medical device of claim 13, wherein the actuator includes at least two arms, wherein each of the at least two arms has an external surface configured to matingly cooperate with an internal surface of the grip.

15. The medical device of claim 10, wherein the stabilizer is configured to be rotatably coupled to an insertion device.

16. A medical device, comprising:
    a C-shaped stabilizer configured to be coupled to a port of an insertion device;
    a shaft configured for telescopic translation within the stabilizer, wherein the shaft includes a pair of protrusions extending radially outwardly from a sidewall thereof;
    a grip coupled to the shaft; and
    an actuator coupled to the grip, wherein the actuator is axially moveable relative to the grip so as to selectively actuate a distal assembly of the medical device, wherein the actuator includes at least one arm, wherein the at least one arm has an external surface configured to matingly cooperate with an internal surface of the grip.

17. The medical device of claim 16, wherein the actuator includes at least two arms, wherein each of the at least two arms has an external surface configured to matingly cooperate with an internal surface of the grip.

18. The medical device of claim 16, wherein the stabilizer is configured to be rotatably coupled to an insertion device.

* * * * *